(12) United States Patent
Kuo

(10) Patent No.: US 7,314,453 B2
(45) Date of Patent: Jan. 1, 2008

(54) HANDHELD DIAGNOSTIC DEVICE WITH RENEWABLE BIOSENSOR

(76) Inventor: Youti Kuo, 88 Foxbourne Rd., Penfield, NY (US) 14526

( * ) Notice: Subject to any disclaimer, the term of this patent is extended or adjusted under 35 U.S.C. 154(b) by 941 days.

(21) Appl. No.: 09/853,803

(22) Filed: May 14, 2001

(65) Prior Publication Data

US 2003/0023189 A1 Jan. 30, 2003

(51) Int. Cl.
*A61B 5/00* (2006.01)
*B65D 81/00* (2006.01)
(52) U.S. Cl. ...................... 600/584; 600/309
(58) Field of Classification Search ........ 600/573–584, 600/310, 309, 345, 349
See application file for complete search history.

(56) References Cited

U.S. PATENT DOCUMENTS

| | | | |
|---|---|---|---|
| 3,968,011 A | 7/1976 | Manautou et al. | 435/18 |
| 4,981,786 A | 1/1991 | Dafforn | 435/7.92 |
| 5,047,206 A | 9/1991 | Dombrowski | 422/56 |
| 5,077,199 A | 12/1991 | Basagni et al. | 435/14 |
| 5,100,620 A | 3/1992 | Brenneman | 422/58 |
| 5,120,420 A | 6/1992 | Nankai et al. | 204/403 |
| 5,206,711 A | 4/1993 | Bethold et al. | 356/436 |
| 5,208,147 A | 5/1993 | Kagenow et al. | 435/14 |
| 5,264,103 A | 11/1993 | Yoshioka et al. | 204/403 |
| 5,335,305 A | 8/1994 | Kosa | 385/147 |
| 5,531,878 A | 7/1996 | Vadgama | 204/415 |
| 5,567,290 A | 10/1996 | Vadgama et al. | 204/415 |
| 5,573,798 A | 11/1996 | Kato | 427/126.5 |
| 5,684,296 A | 11/1997 | Hamblin | 250/227.11 |
| 5,739,041 A | 4/1998 | Nazareth et al. | 436/518 |
| 5,851,838 A | 12/1998 | Vetter et al. | 436/170 |
| 5,866,352 A | 2/1999 | Vorberg | 435/25 |
| 5,869,003 A | 2/1999 | Nason | 422/58 |
| 5,876,952 A | 3/1999 | Shieh | 435/141 |
| 5,879,635 A | 3/1999 | Nason | 422/102 |
| 5,906,719 A | 5/1999 | Treloar et al. | 204/415 |
| 5,909,977 A | 6/1999 | Kuo | 401/146 |
| 5,988,426 A | 11/1999 | Stern | 220/371 |
| 5,997,817 A | 12/1999 | Crismore et al. | 422/58 |
| 6,004,441 A | 12/1999 | Fugiwara et al. | 204/412 |
| 6,019,734 A | 2/2000 | Parkinson | 600/572 |
| 6,027,570 A | 2/2000 | Farr et al. | 134/2 |

(Continued)

*Primary Examiner*—Max F. Hindenburg
*Assistant Examiner*—Jonathan Foreman

(57) ABSTRACT

A handheld diagnostic device having a test head and a handle is equipped with an open test channel having sensors and liquid reagent dispensing opening for the diagnostic testing of body fluids. The test channel can draw in fluid sample by capillary force and be closed by a channel cover for mixing the fluid sample with liquid reagent for electrochemical reactions for providing measurement signals for diagnostic analysis by a microprocessor included in the handle. A vibration means is added for stimulating the production of the body fluid sample and for assisting mixing of the sample solution. A renewable biosensor having a reusable electrode system and a dispensing means for providing a new dose of liquid reagent is included in the test head for repeated uses of the test channel and the biosensor. A dual-dispensers system having two reagent cartridges and two dispensing lines is included for simultaneous or selective dispensing of reagents for multiple diagnostic testing. The handheld device can be used for the self-diagnostic testing of saliva, body fluid, blood and vagina fluid for home healthcare and for monitoring predetermined components in a pourable fluid. For vagina fluid applications, a handheld diagnostic device may include cream or foam dispenser for dispensing vagina medication material, lubricant, or spermicide.

10 Claims, 24 Drawing Sheets

U.S. PATENT DOCUMENTS

| | | | |
|---|---|---|---|
| 6,043,878 A | 3/2000 | Gratzl et al. | 356/246 |
| 6,058,934 A | 5/2000 | Sullivan | 204/409 |
| 6,066,243 A | 5/2000 | Anderson et al. | 204/403 |
| 6,071,739 A | 6/2000 | Vadgama | 435/287.9 |
| 6,080,118 A | 6/2000 | Blythe | 600/591 |
| 6,087,182 A | 7/2000 | Jeng et al. | 436/66 |
| 6,099,484 A | 8/2000 | Douglas et al. | 600/583 |
| 6,106,461 A | 8/2000 | Roskin et al. | 600/309 |
| 6,174,293 B1 | 1/2001 | Buck et al. | 600/572 |
| 6,176,903 B1 | 1/2001 | Wamsiedler | 96/208 |
| 6,183,428 B1 | 2/2001 | Kilgore | 601/70 |
| 6,623,698 B2 * | 9/2003 | Kuo | 422/68.1 |

* cited by examiner

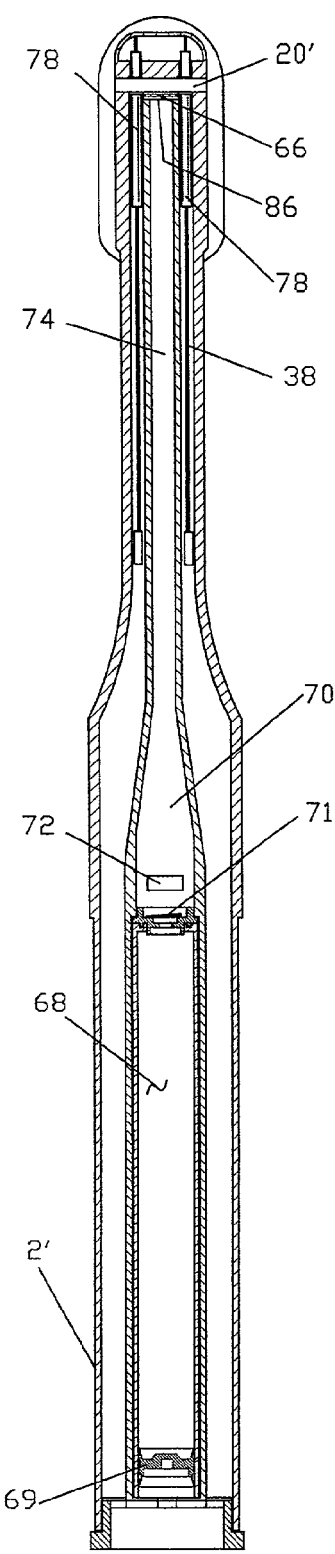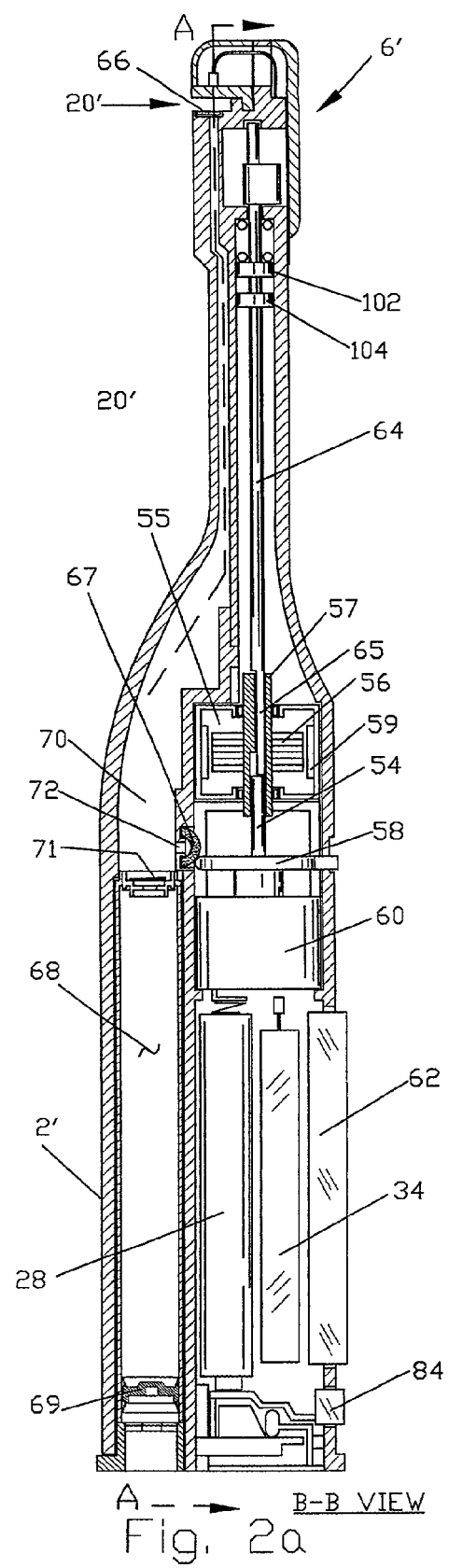
A-A VIEW
Fig. 2b
B-B VIEW
Fig. 2a

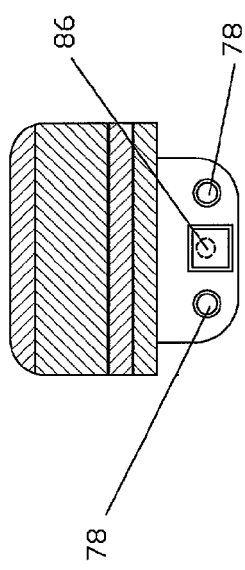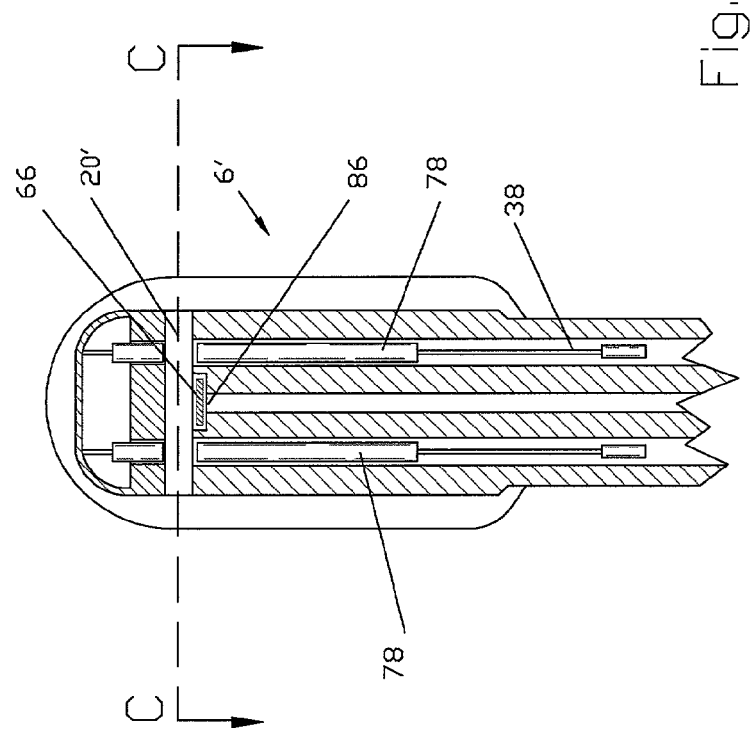

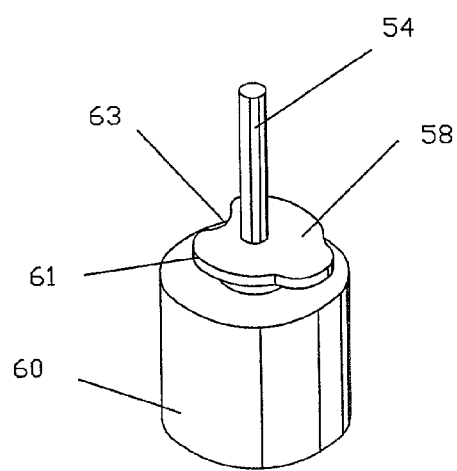
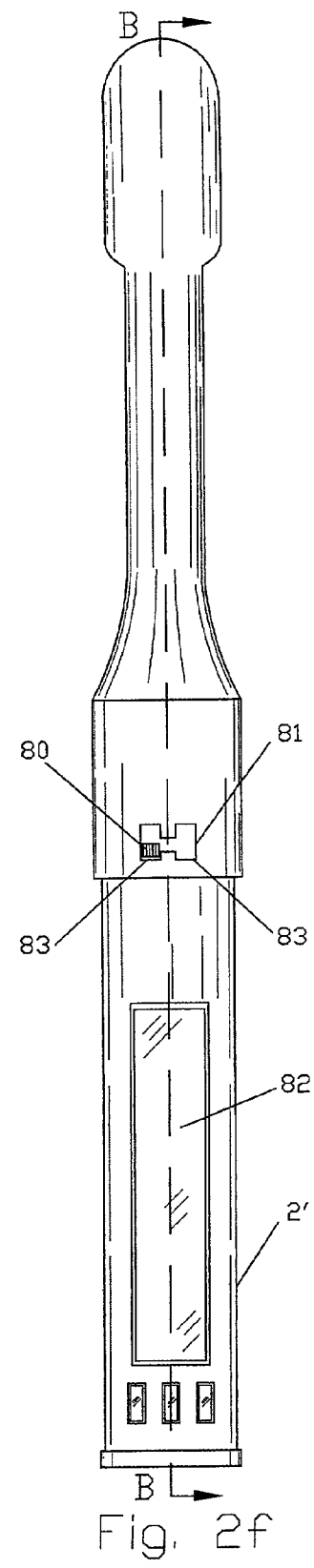
Fig. 2e
Fig. 2f

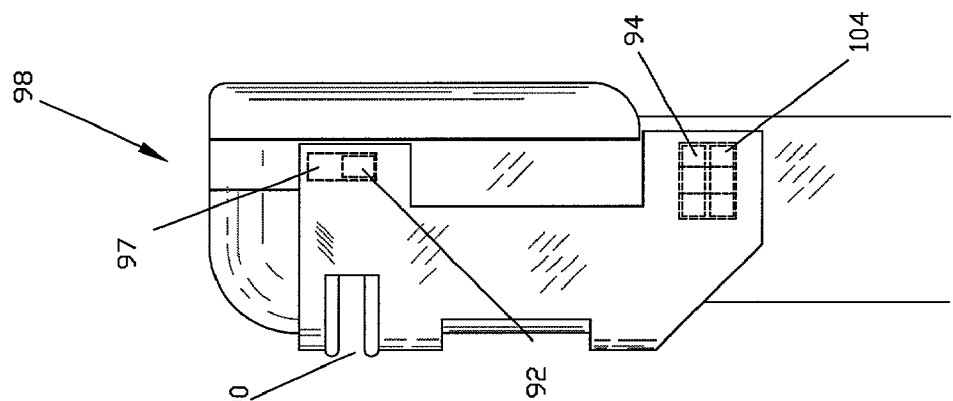
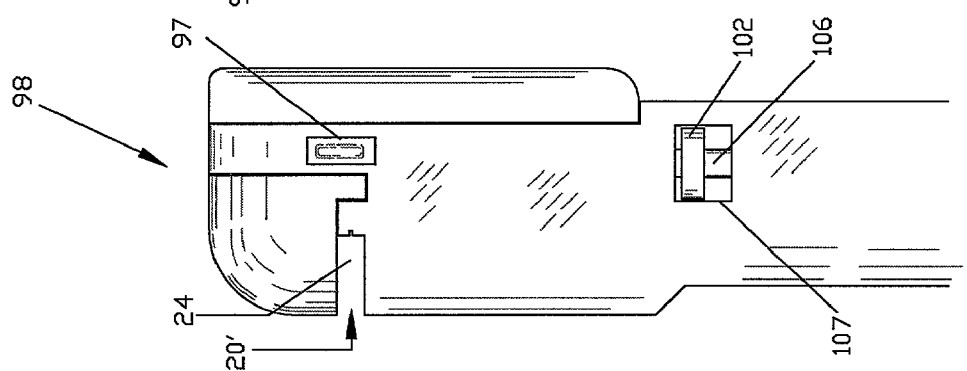
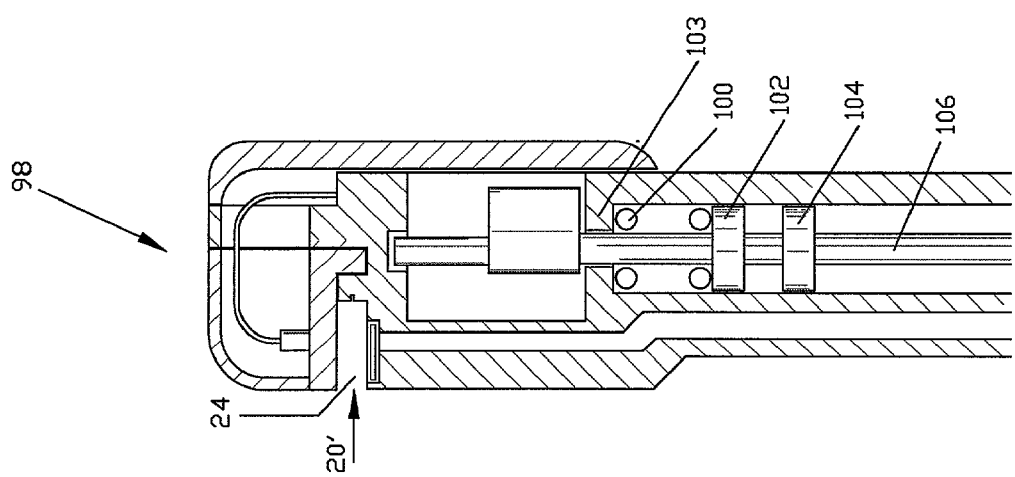
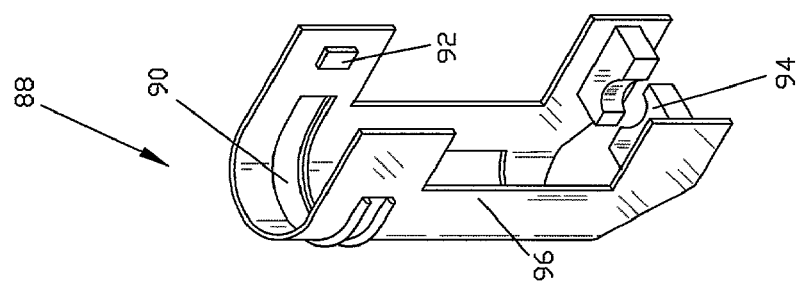

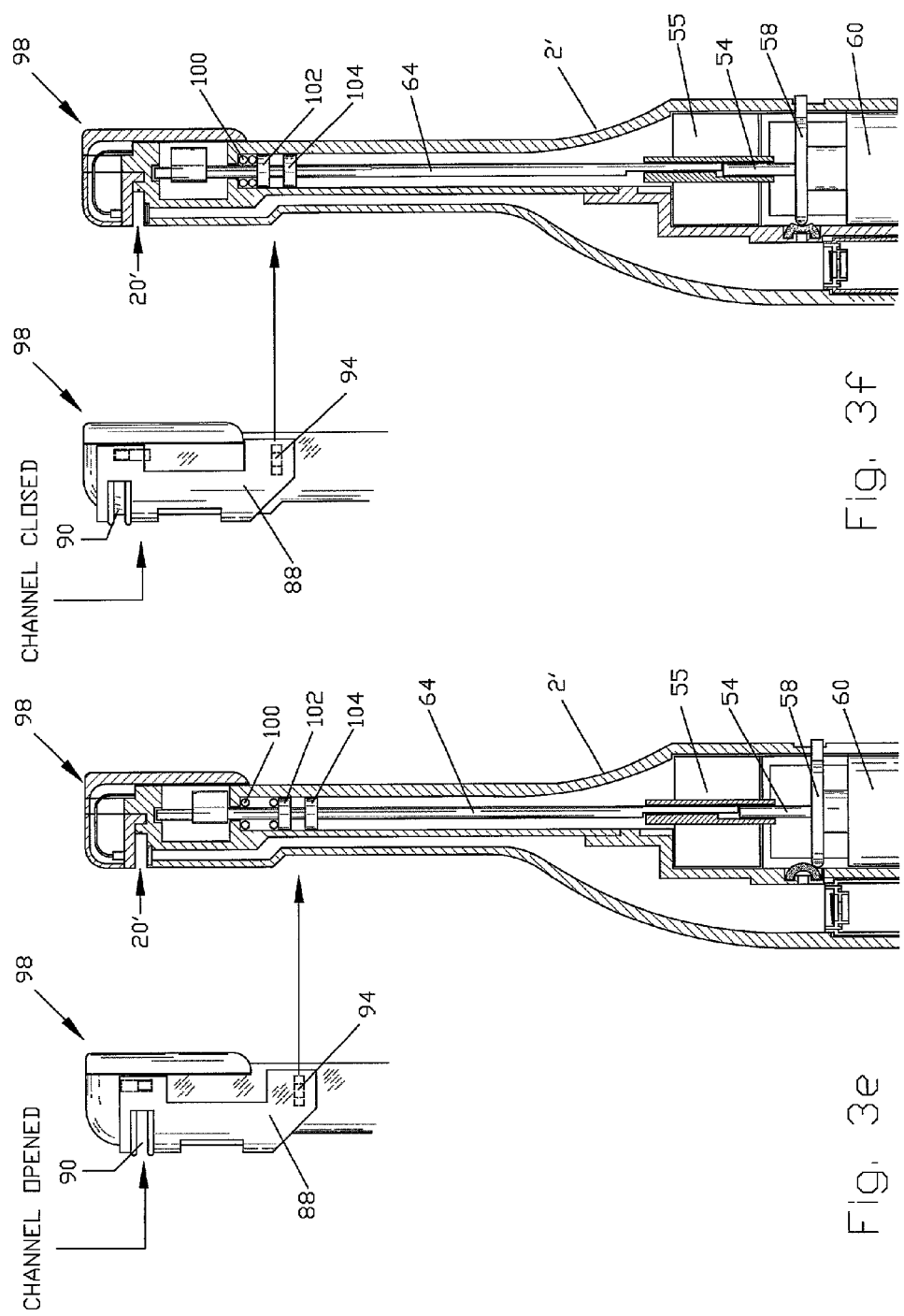

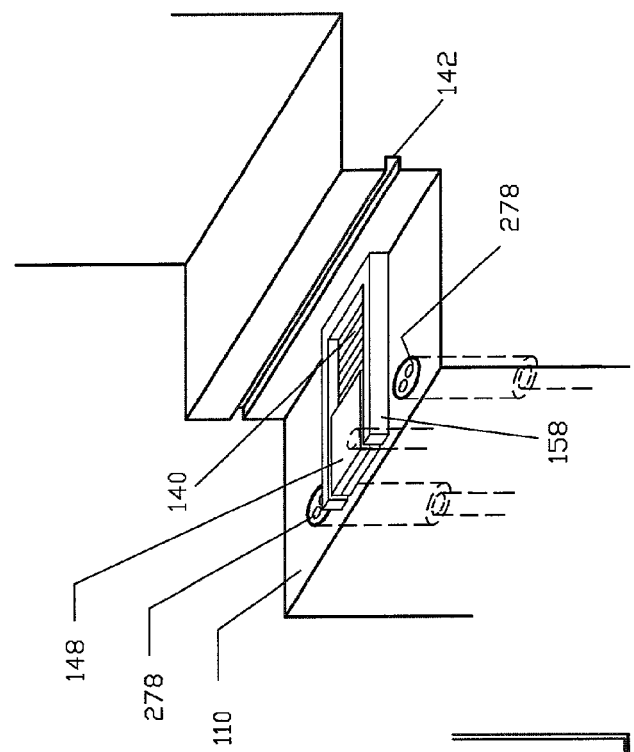
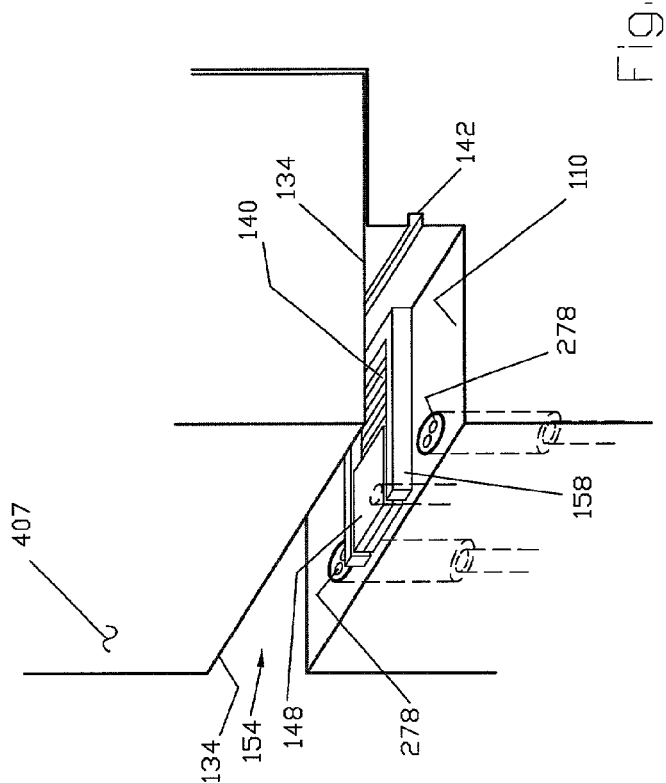

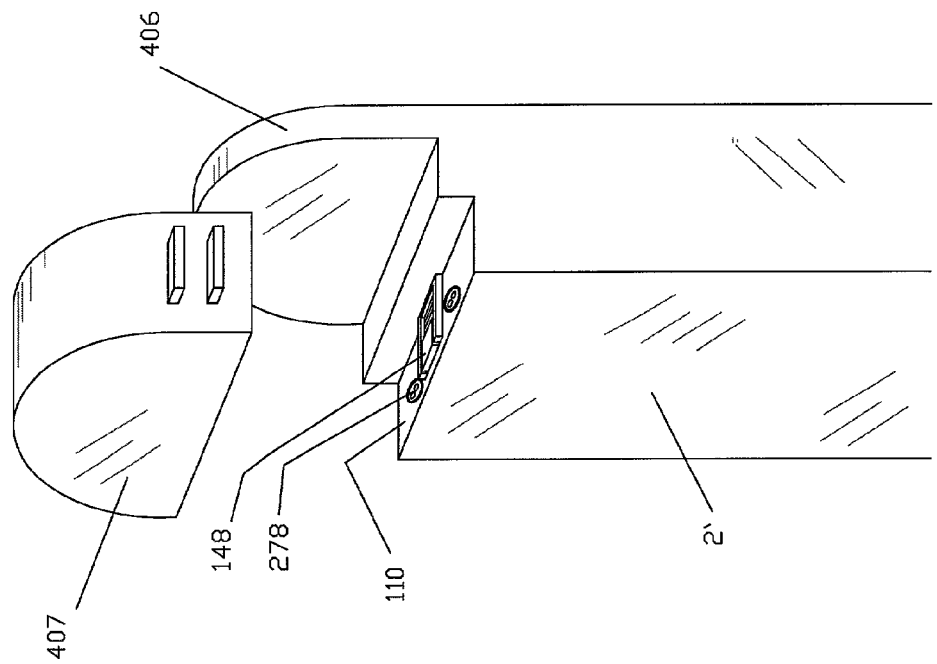
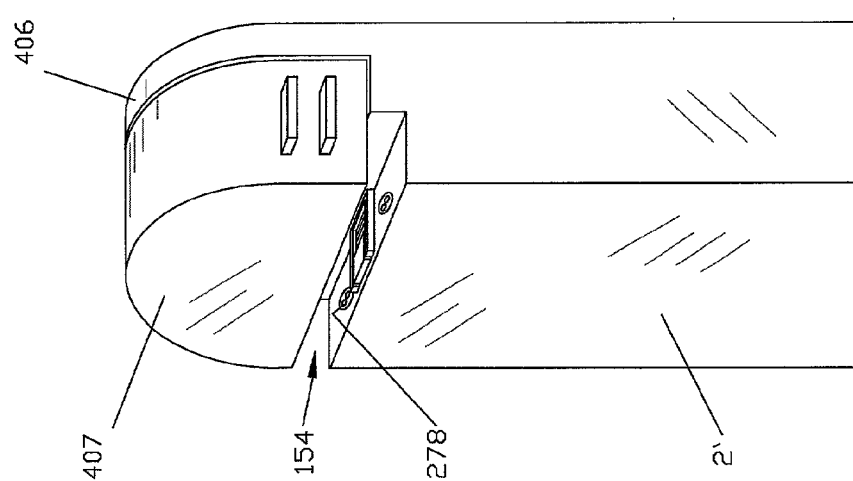

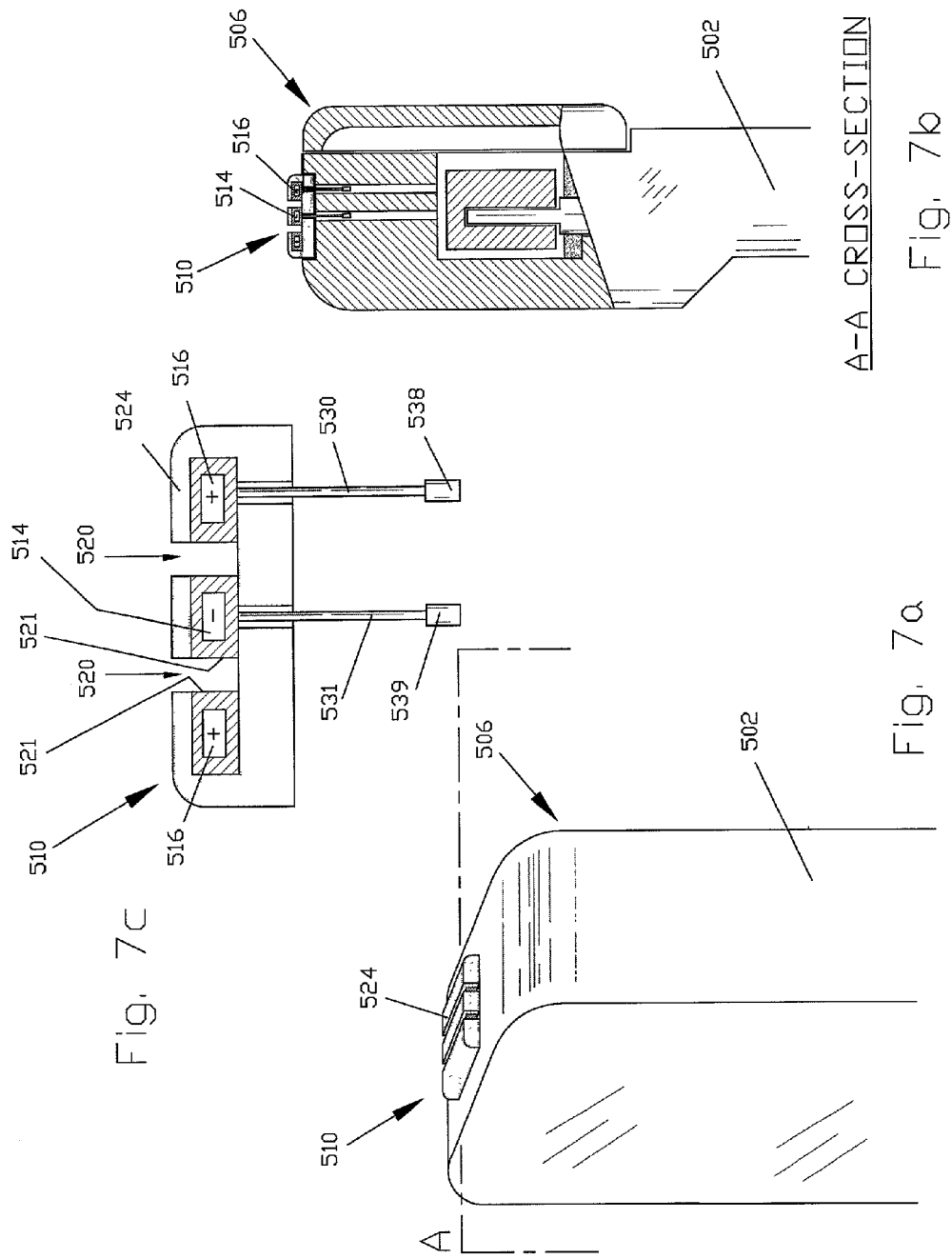

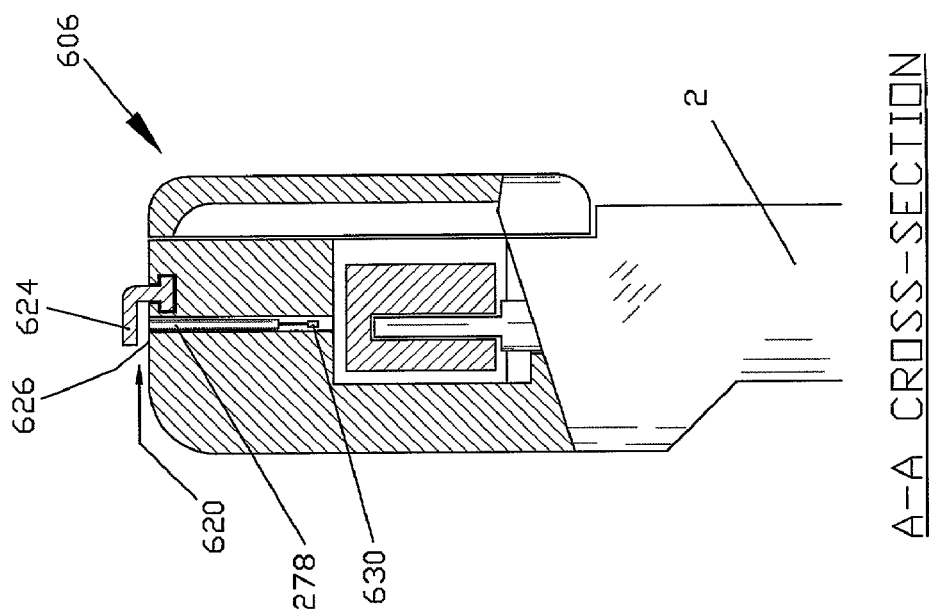
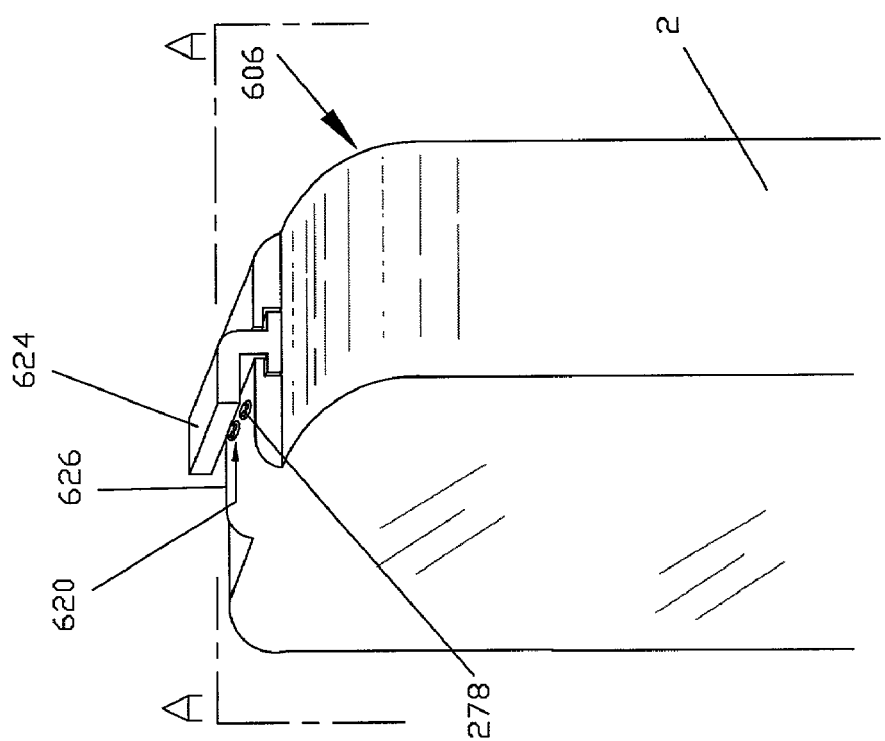

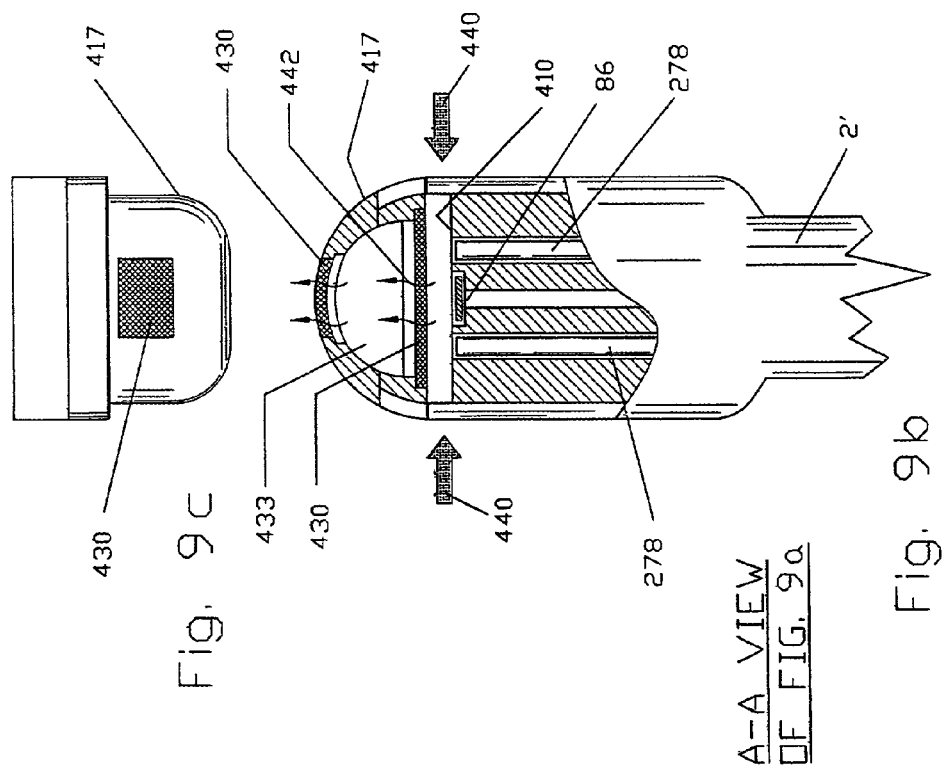
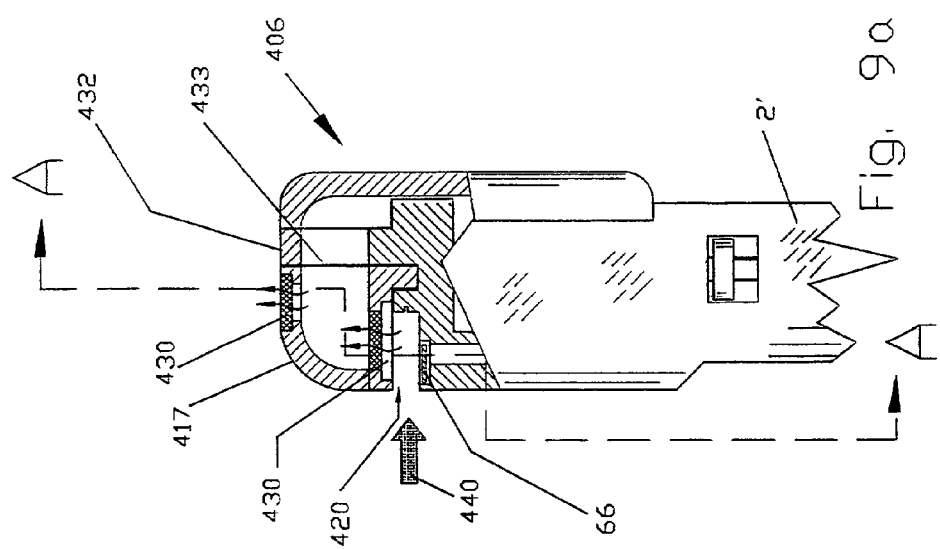

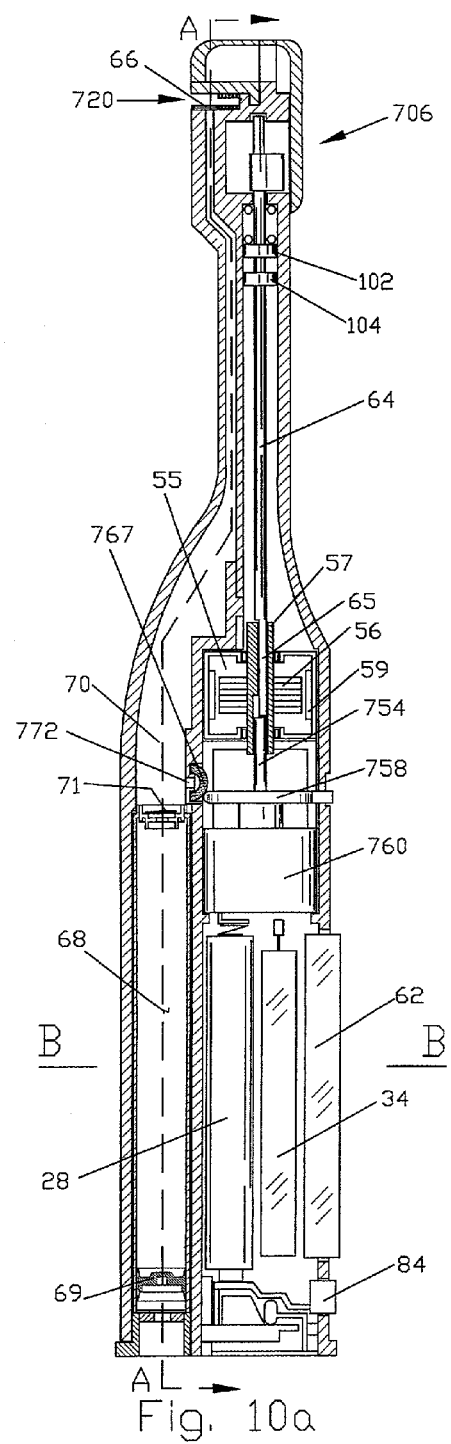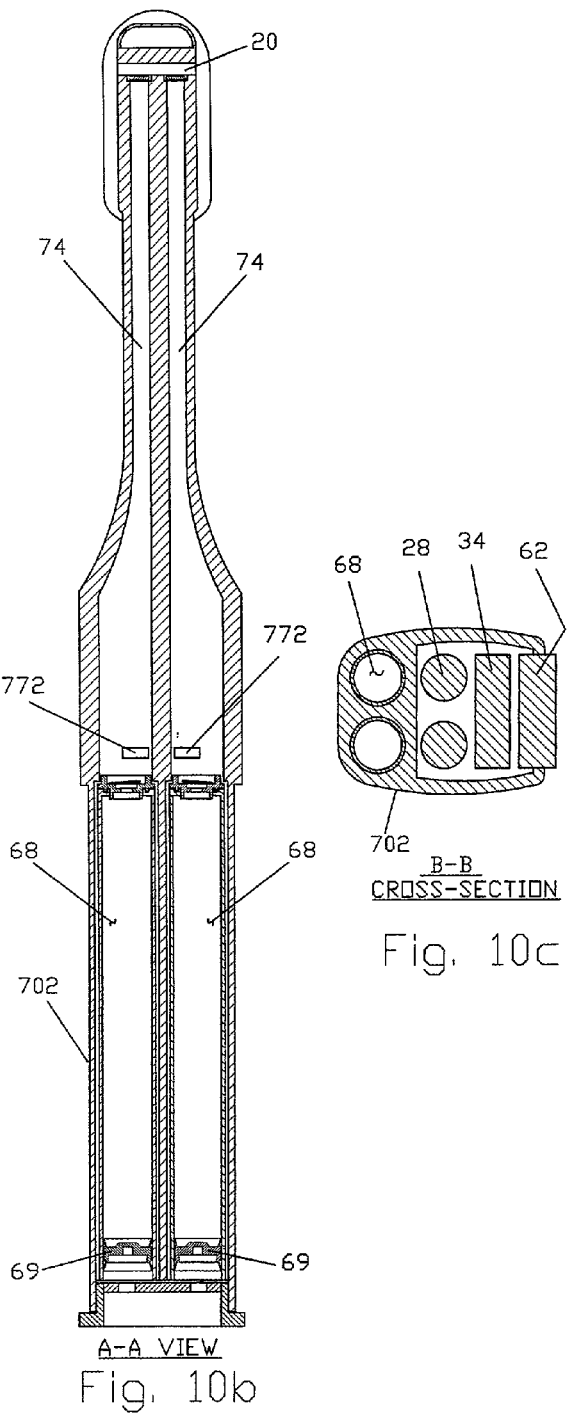
Fig. 10a
Fig. 10b
B-B CROSS-SECTION
Fig. 10c

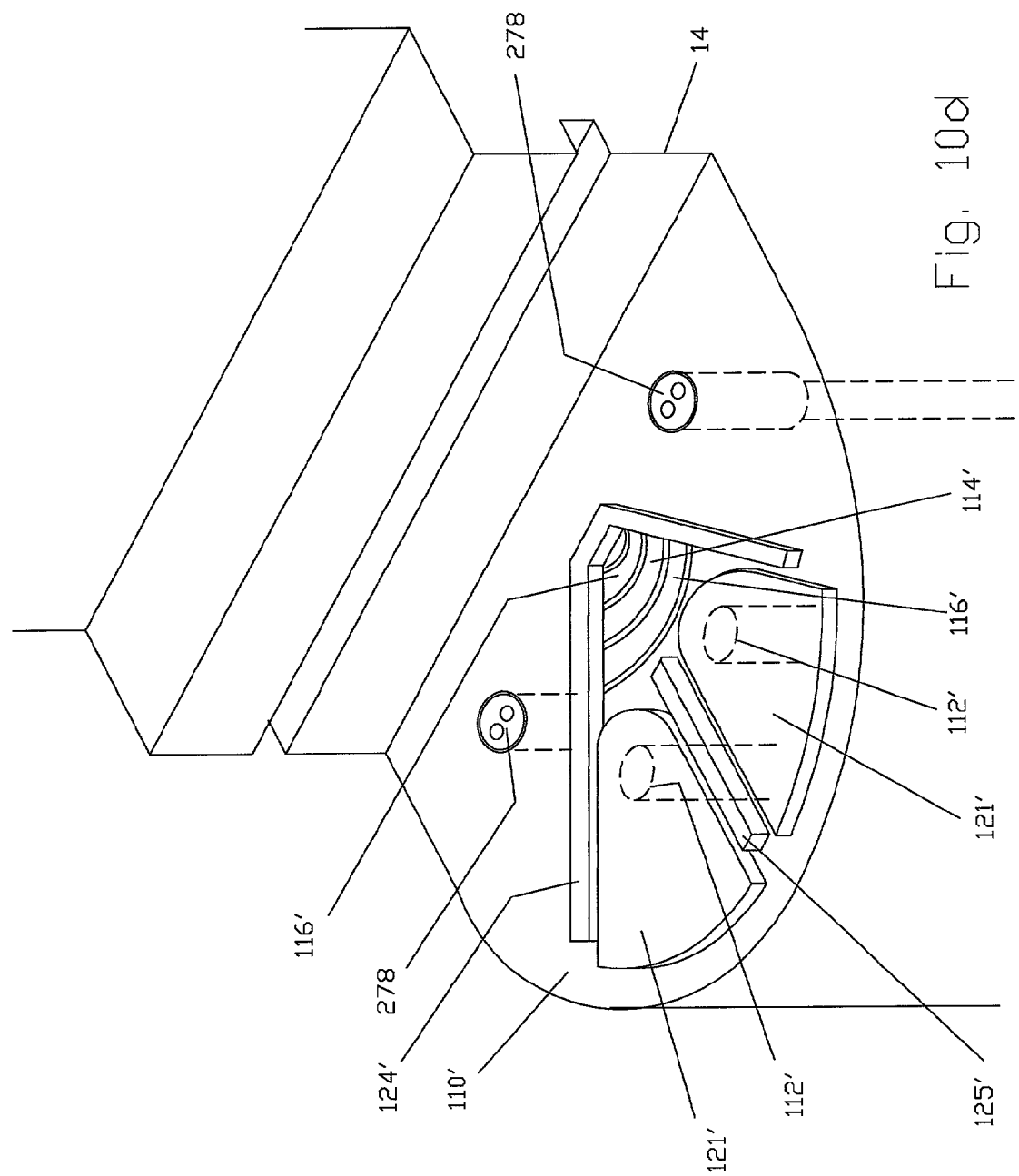

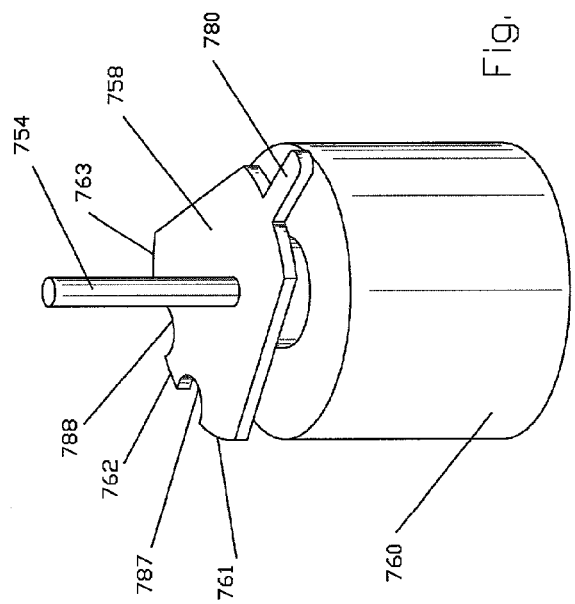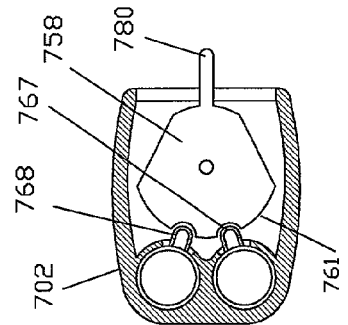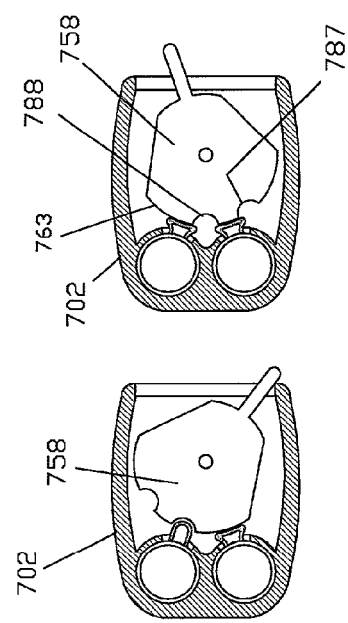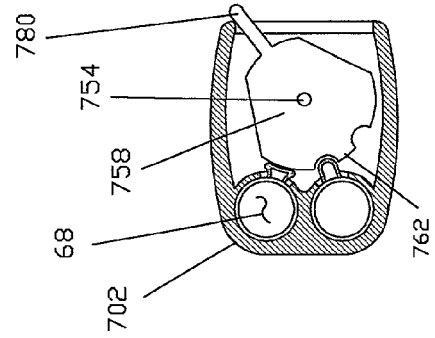

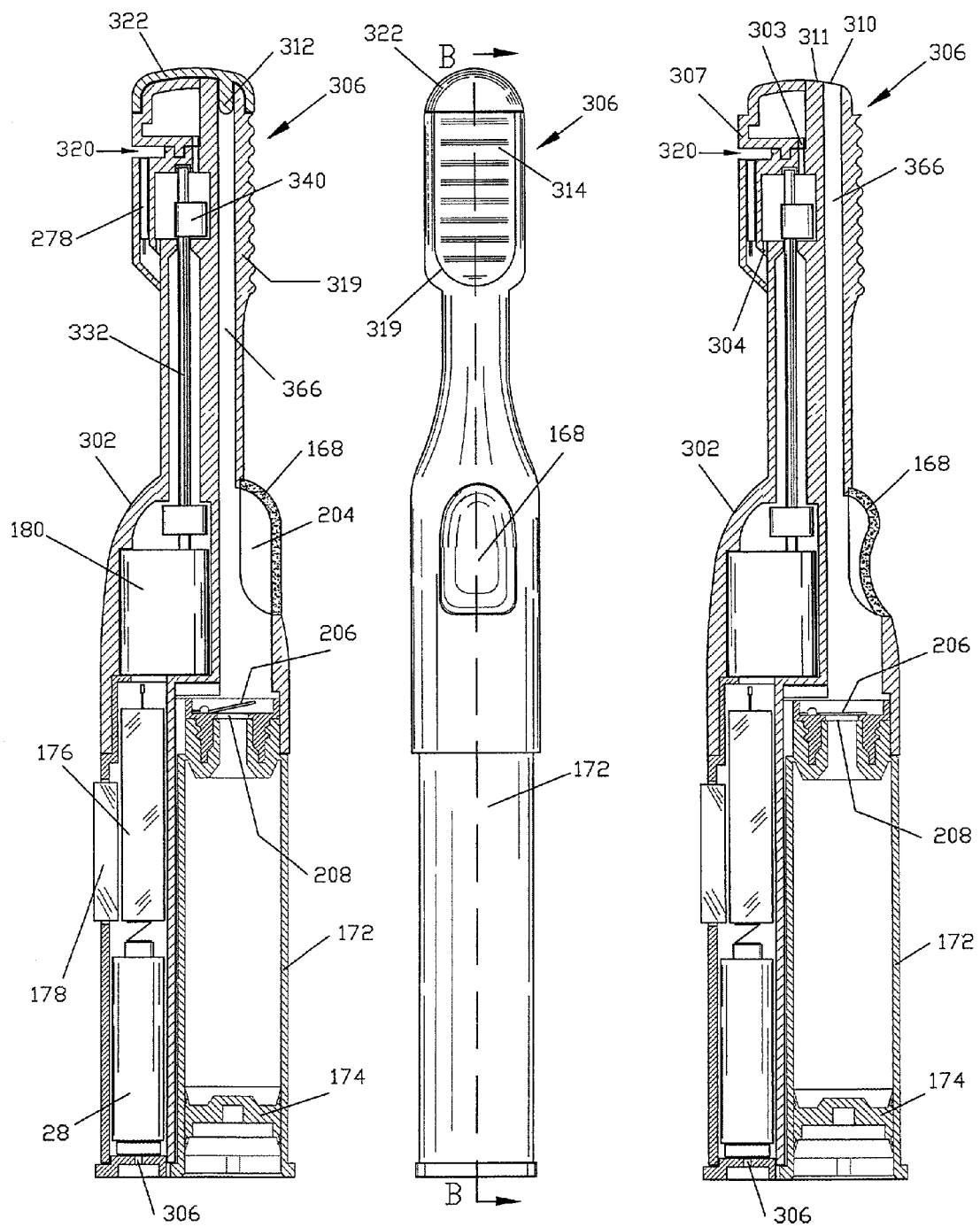

HANDHELD DIAGNOSTIC DEVICE WITH RENEWABLE BIOSENSOR

BACKGROUND OF THE INVENTION

There is a growing need for home monitoring and diagnosis of body fluids for the early detection of health problems and for reducing health care costs. A handheld diagnostic device is desirable for collecting body fluids in a test channel for in situ testing with self-contained sensors and microprocessor for diagnosis. Such a handheld diagnostic devices also needs to include liquid reagent dispensing means and a renewable biosensor for repeated routine testing in a reusable test channel, which can be easily cleaned.

(1) Field of the Invention

The present invention relates to handheld body fluid diagnostic devices with liquid reagent dispensing capability.

(2) Related Art

There are a number of patents in the prior art that deal with the diagnosis of body fluids and related test sample collection methods and sensor configurations. In the following patents of interest on the diagnosis of urine, vagina fluid, and blood as well as on the collection and measurement of test samples are summarized for reference.

Urine

U.S. Pat. No. 5,739,041 by Nazareth et al. describes an urine collection and diagnostic device. The device receives urine sample directly from the urine stream and uses an assay material comprising a release medium of a visually detectable analyte binding reagent for detecting an analyte in the urine sample. The patent provides results of pregnancy test for assessing the measurement accuracy of the device. Although the device uses drainage vents to eliminate the incident of flooding to improve the reliability of test results, the flow path of the device is not an open channel type to enable cleaning and reuse of the device.

U.S. Pat. No. 5,876,952 by Shieh provides an amperometric glucose biosensor for the rapid detection of glucose in an urine sample. The glucose biosensor employs a sandwich configuration by which a reagent strip is placed between a sensing electrode and a reference electrode layer. When in contact with a drop of urine, the sensor provides current signal of the test sample for converting to units of urine glucose concentration, which has a linear relationship with the blood glucose concentration. This reagent strip-type glucose biosensor is for one time use only, not for low costs and frequent regular uses.

U.S. Pat. No. 6,027,570 by Farr, et al. discloses a method for cleaning optical surfaces which are repeatedly used in a urine analyzer. The method uses an aqueous solution of a quaternary ammonium or phosphonium salt, a non-ionic surfactant and a divalent ion. The clarity of the urine as related to the presence of white or red blood cells and epithelial cells orbacteria can be determined by measuring the refractive index of the urine sample through an optical surface. An optical surface is made of acrylic or other transparent material such as glass. The use of the cleaning solution ensures that the optic be cleaned without residue of urine sample affecting the refractive index for repeated measurements. For determining concentration values of glucose and other analytes, U.S. Pat. No. 6,087,182 by Jeng et al. developes a reagentless analysis of biological samples particularly suitable for urine. It uses spectroscopic measurements, visible and infrared light absorption spectroscopy to quantify the concentration of one or more analytes in a biological sample with mathematical techniques. The methods as described for measuring refractive index require the use of visible and infrared spectrometers which are too complex to be practical for a handheld diagnostic device. However, the methods demonstrate the feasibility of determining broad range of analytes without using reagents for diagnosis.

Vagina fluid

On testing vagina secretion, U.S. Pat. No. 6,106,461 by Roskin et al. uses a pH indicating material attached to panty liners and the like for differentiating between yeast and non yeast vaginal infections, as well as for diagnosis of bacteria, viruses and other microorganisms. The pH indicating material is of the type that provides a color indicative of the pH of the fluid in contact. The method depends on undefined quantity of absorbed vagina secretion on the panty liner and the visual comparison of observed color with a given color chart, both of which are subject to measurement and reading errors. More quantity of vaginal fluid sample is used in U.S. Pat. No. 6,174,293 by Buck et al. as it uses an absorbent media for collecting vagina fluid and then extracting the fluid for diagnostic purposes. For intra vaginal collection, the absorbent media is placed in a housing having receiving apertures prior to insertion into the vagina. The absorbent media is shaped similar to a tampon and it includes an absorbent core, which is at least partially surrounded by a porous matrix. The patent does not describe the procedures of extracting the fluid from the absorbent media and the diagnosis of the test sample. A more specific testing procedure is described in U.S. Pat. No. 6,019,734 by Parkinson, which simplifies the diagnosis of bacterial vaginosis. The simplified diagnostic kit includes a pH strip and a potassium hydroxide ("KOH") patch for detecting bacterially derived amines. However, the kit is for one time use in a doctor's office only, not re-useable and not for self-diagnostic at a home environment.

In response to women who suffer menstrual cramps and vagina dryness, U.S. Pat. No. 6,183,428 by Kilgore describes the use of a built-in vibration mechanism in a tampon apparatus for easing the insertion of a tampon and menstrual cramps. Separately U.S. Pat. No. 6,080,118 by Blythe also describes the benefit of vagina stimulation for generating vagina fluid for testing but it does not address the requirement of containing a fixed amount of fluid sample for quantitative diagnostic measurements.

Blood

On diagnosis of blood samples, U.S. Pat. No. 5,077,199 by Basagni, et al. provides a stable unitary ready-to-use liquid reagent for determining the glucose content in blood. The liquid reagent comprises a glucose-oxidase free from catalase and a nonionic surface-active agent as a stabilizer. For increasing the shelve life, two reagents remain separated prior to mixing with a test sample. U.S. Pat. No. 5,866,352 by Vorberg develops a kit of two liquid reagent components for determining the fructosamine content related to glucose of a blood sample measured by color change. A test sample is treated to remove interfering sample components at a nearly neutral pH by a first reagent, and then to set a basic pH by a second reagent for producing color reaction. The method as described in the patent deals with pre-mixing of the first and the second reagents before adding with the test sample, The rate of change of color at an appropriate is photometrically determined and compared to that of a calibrating solution. This desirable process demonstrates the need of a diagnostic device having a dual-reagents dispensing capability.

Test Sample Collection

For testing body fluid samples in general, U.S. Pat. No. 4,981,786 by Dafforn discloses an assay device having multiple ports for transporting a fluid sample into contact with a reagent by the capillary action of a bibulous strip. The bibulous strip has one or more immunosorbing zones for controlling the volume of the fluid that traverses the immunosorbing zones. It uses a scale in a transparent window for quantifying the analyte in the test sample. The configuration as described, however, is only applicable to the delivery of the test sample by a dropper, syringe needle or the like, not for collection of test sample directly from a pool of body fluid.

In a more elaborate testing system, U.S. Pat. No. 6,066,243 by Anderson, et al. provides with a portable device having multiple removable testing modules for analyzing selected characteristics of body fluid samples. The portal diagnostic device includes sample chambers with inlet ports, sensors and electrical interface components, in situ calibration media, disposable cartridges and reagent test strips. The combination of the signal processing unit, the circuitry and module interface units enables direct utilization of the output signals of the removable modules for providing visual or printed display of the measured characteristics of the test samples. Although the device is portable, it is not as convenient as a handheld device and it does not simplify the process of collecting body fluids for testing.

Other liquid reagent dispensing means are described in the testing of medical swabs. U.S. Pat. No. 5,869,003 and 5,879,635 by Nason describe testing of medical swabs with liquid reagents. The former patent uses a dispenser cap to deliver one or more reagents to for contacting a collected specimen and causing a portion of the specimen to flow through a transfer wick to a diagnostic strip. The flow of the mixed specimen and reagent from the specimen chamber is directed by a valve to contact with a transfer wick which has multiple fingers impregnated with different reagents. The latter patent uses a dual-nib reagent dispenser for dispensing multiple reagents. The dual-nib dispenser is deformable to dispense two reagents in a manner to pre-mix the two reagents in a reagent chamber. The mixed reagents then is dispensed to contact a specimen for testing. While both of these methods provide testing means for medical swabs with multiple reagents, the amount of a reagent or mixed reagents in contact with the specimen is not controlled. Moreover, the disclosed dual-nib reagent dispenser does not have the flexibility of dispensing reagents independently into a test chamber.

Measurements of Test Sample

An in-situ testing procedure with direct contact between a test fluid and sensors without utilization of a third medium for transporting or extraction has been described in the above-mentioned U.S. Pat. No. 6,080,118 by Blythe for testing the vagina secretion. It uses a tubular probe for inserting into the vagina channel for immersing sensors in the vagina fluid for measurements. The insertable portion of a vaginal probe includes a number of fluid flow grooves and the probe is rotatable for stimulating the secretion of vaginal fluids for collection. The sensors are electronically coupled to integrated circuitry for analyzing measured data and are mounted on the surface of the vaginal probe to test a non-controlled quantity of test fluid between the sensors and the vaginal wall. The inconsistency of the volume of the test fluid can lead to significant measurement errors.

U.S. Pat. No. 5,684,296 by Hamblin describes a fiber optic liquid sensing system. The system uses a reflective-type optical sensor which has a housing with a highly polished reflector. The reflector is positioned at a distance opposed to the terminal surfaces of light emitting and a light receiving strands, which are bundled in side-by-side fashion. There are a number of apertures on the circumferencial wall of the housing for drawing in a fluid sample for optical measurements. Although the sensor housing is compact and contains all the sensor components, the configuration of the apertures may entrap air inside the housing that causes measurement errors. Because the segmented walls between the apertures hinder thorough cleaning, the sensor is non-reusable.

U.S. Pat. No. 5,206,711 by Bethold et al uses an open channel in conjunction with a fluid opacity sensor for measuring opacity of a fluid sample in a process line. To compensate for light source drift caused by temperature effect and 60 Hz line noise in the processing electronics, a reference optical pathway having the same optical system is used and a signal processing means is provided to cancel the effects of the light source drift. The width of the channel used is designed for the passage of fluid rather than for inducing a capillary effect to draw in and hold a fixed volume of sample fluid for testing. U.S. Pat. No. 6,043,878 by Gratzl et al. describes optical measurement systems for measuring optical property of a microliter size (droplet) test sample and a gas-assisted mixing system for mixing and stiring the test sample with an incoming reagent which is diffused through a membrane. The measurement systems as described do not control the height of sample droplet, therefore, the variation of droplet profile may affect the accuracy of reflective measurement by the optical sensor. Moreover, the slow diffusion of the reagent through the membrane and the required gas flow for mixing are not practical for a handheld diagnostic device.

U.S. Pat. No. 6,099,484 by Douglas et al. discloses a capillary tube for drawing body fluid from an incision and a test strip affixed to an upper end of the capillary tube for receiving the fluid. By pressing the device against the skin at the site of an incision, the test strip directly contacts body fluid emanating from the incision. To ensure that a sufficient sample size enters the tube, a drop-detecting mechanism uses either electrodes or an optical system for detecting the height of the sample drop. Similarly, U.S. Pat. No. 5,100,620 by Brenneman uses a capillary tube in conjunction with an exposed reagent pad to contact a test fluid. A vent passageway having a smaller diameter than the capillary tube is also used. Optical measurement begins as the optics system senses the start of a change in color of the reagent pad. Since both methods employ a capillary tube of small diameter (ranging from 0.01 to 0.03 inches), the fluid inside the tube cannot be washed out to clean it for repeated uses.

There are many prior art patents aim at even coverage of a blood sample on a reagent layer for testing. U.S. Pat. No. 5,047,206 by Dombrowski illustrates a reagent test strip having a cover mounted over an insoluble reagent surface for defining a capillary chamber for drawing a predetermined amount of liquid for quantitative measurement of the reflectance of the reagent surface. The capillary chamber has two open ends over the reagent surface but having no means of detecting the timing of complete filling the test chamber. Although a fixed amount of liquid sample is used, the test sample is not ensured mixed with the insoluble reagent and it requires much longer measurement time compared to that of a liquid reagent, which can be well mixed with a liquid sample.

U.S. Pat. No. 5,851,838 by Vetter et al uses a planar capillary gap for transporting a sample fluid over the top of a diagnostic test carrier. To avoid false test results caused by continuous re-diffusion of analyte out of a test area while the test reaction is in progress, the patentee uses excess sample liquid to surround the test carrier. Since the capillary gap is not closed during testing, the test is subject to measurement errors. Although each of these patents demonstrates use of a capillary tube for transporting a fluid sample over a test strip for testing, the capillary channels and test strips are manually replaced for each use. This is inconvenient and costly for use in a home diagnostic device.

Sensors suitable for use in conjunction with small spaces such as a capillary test channel are known. U.S. Pat. No. 5,335,305 by Kosa discloses fabrication methods for installing fiber optical sensors in fiber bundles fabricated from fibers that are bent with small radii. U.S. Pat. No. 5,851,838 by Vetter et al., U.S. Pat. No. 5,997,817 by Crismore et al., and U.S. Pat. No. 6,058,934 by Sullivan show various electrode matrices arranged in planar configurations. Sullivan details the use of four terminals in which voltage measuring electrodes are separated from current carrying electrodes, enabling only a low current to be drawn from a sample. The arrangement confines the measured current to the sensor chamber, thereby preventing the conductivity sensor from interfering with other sensors in the test instrument. The patentee describes the advantage of using a planar configuration to simplify the manufacturing process and enhance efficient fluidics so that the cells can be filled and washed out with a minimal volume of reagent. The size of the chip may be, for example, approximately 0.12 by 0.12 inches and can be disposed in a flow cell receptacle in a sensor housing to form one wall of a fluid flow path on which fluid flows perpendicular to the parallel arrangement of the electrodes. The width and spacing of the electrodes are not critical, each typically being 0.005 inches. The Crismore et al patent discloses the use of palladium as the electrode surface because of its resistance to oxidization and its relatively low cost. The preferable distance between electrodes is about 1.2 mm and the exposed area of an electrode need not be entirely covered with a test reagent.

Electrodes can also be used to measure pH. U.S. Pat. No. 5,573,798 by Kato relates to a pH-measuring electrode having a sensor film of metal oxide, which is sensitive to a hydrogen ion in solution. In operation, the pH-measuring electrode is immersed in the solution to be measured together with a reference electrode such as a calomel electrode or a silver-silver chloride electrode. Based on the potential difference between the two electrodes, a pH value is determined.

The combined use of an electrode system with a dry reagent layer for testing physiological fluids has been the subject of several patents on biosensors including U.S. Pat. No. 5,120,420 by Nankai et al., U.S. Pat. No. 5,264,103 by Yoshioka et al. and U.S. Pat. No. 6,004,441 by Fugiwara et al. Using blood drops as test samples for detecting glucose, the biosensors disclosed in these patents utilize an electrode system produced by screen-printing and a dry reagent layer containing an enzyme which reacts only to glucose in the blood sample. The enzyme contained in the reagent layer is dissolved in the sample liquid. According to the description contained in U.S. Pat. No. 6,004,441 by Fugiwarra et al, the electrode system of a biosensor is comprised of an electrode for measurement and a counter-electrode which functions as a reference electrode. The covering on top of the electrode system is a reagent layer which includes glucose oxidase as an enzyme and potassium ferricyanide as a mediator. When a voltage is applied between the electrodes, electric current flows in proportion to the concentration of glucose. Typical dimensions of an electrode system are 5 to 10 nm in electrode thickness and about 70. mu.m between electrodes. For better performance, the width of each of the two counter-electrodes is preferably the same or larger than that of the measuring electrode. In operation, a drop of blood is placed on the reagent layer after the electrode system is energized. After the change in conductivity stabilizes, the voltage applied is suspended for a period of time to allow for the oxidation of glucose and the reduction of potassium ferricyanide to take place. After completion of the reaction, a voltage is applied again to cause oxidation of the reduced potassium ferricyanide. This results in an electric current, which is proportional to the concentration of glucose, as a measurement of the blood sugar level.

It is well known in the prior art to cover the electrode surfaces of a biosensor with permselective membranes to separate a fluid sample from contacting the electrodes directly. The main function of a permselective membrane is to separate electrolytes for electrochemical reactions from interferants in a fluid sample that induce measurement errors. U.S. Pat. No. 5,567,290 by Vadgama uses un-plasticized polyvinyl chloride (PVC) as a membrane barrier for testing a physiological fluid. The material acts as a barrier to paracetamol and sugars but is permeable to hydrogen peroxide and oxalate for electrochemical reactions. The sensor of U.S. Pat. No. 5,531,878 by Vadgama et al. uses enzyme electrodes incorporating a microporous membrane coated with the carbonaceous material, which is known as "diamond-like carbon". The membrane material is preferably a polycarbonate with thickness preferably less than 10 microns and porosity in the order of 0.05 to 0.01 microns. The coated membrane as an outer shield imparts high resistance to fouling when in contact with a whole blood sample. It extends the linearity of the electrode response over a substantially greater range. Its use in a biosensor enables the reagent-less analysis of an undiluted whole blood for determining the glucose concentration. U.S. Pat. No. 5,906,719 by Treloar et al. describes a permselective membrane incorporating a charged organic species, which provides a conducting path through the membrane between the electrodes of an amperometric sensor. The provision of the organic charge carrier species in the membrane enables current flow between electrodes without interposing a separate liquid or gel electrolyte layer between the electrodes and the membrane. The membrane can be formulated to have a high degree of permselectivity with the use of positively charged organic species for preventing positively charged interferants from entering the membrane. The permselective membranes as described in these patents can extend the linearity of measurement and increase the service life of the electrode sensors.

On the reuse of a biosensor, U.S. Pat. No. 5,208,147 by Kagenow et al. discloses a method for using a disposable measuring device and a conditioning fluid chamber for repeated release of fresh conditioning fluid for calibrating a sensor for measurements. However, the device requires the inconvenient step of moving the sensor to a conditioning fluid chamber to expose the sensor surface to the conditioning fluid. An improved reusable electrochemical sensor is given in U.S. Pat. No. 6,071,739 by Vadgama. The reusable sensor configuration uses a reservoir and a pumping means for dispensing a treatment liquid to a test chamber after testing a fluid sample. The treatment liquid performs cleaning and regeneration of the sensor surface for reuse. Its analyzer system with the reusable sensor utilizes two pivoted body portions having "wallet-like" construction for closing and opening the test chamber. The reusable sensor as described, however, is only for dispensing treatment liquid after closing of the test chamber, not for dispensing a reagent for mixing with a fluid sample in a controllable manner for quantitative measurements.

It is therefore an objective of this invention to provide a handheld diagnostic device having reagent dispensing capability and a renewable biosensor system for the convenience of repeated diagnostic measurements of body fluids at home. It is also an objective of this invention to provide an automatic channel cover for the closing of the test channel for controlling the mixing of a reagent with a test fluid sample for quantitative diagnosis. It is further objective of this invention to provide a dual-dispensers system for simultaneous or selective dispensing of functional fluids for broader diagnostic applications.

SUMMARY OF INVENTION

A handheld diagnostic device having a test head attached to a handle is equipped with an open test channel having sensors and liquid reagent dispensing opening for the diagnostic testing of body fluids. The all-in-one device can collect body fluids internally such as saliva in the mouth and vagina fluid in the vagina channel or externally such as urine in a cup and blood from finger sticking. A reagent for a specific test is stored in a replaceable cartridge inside the handle for mixing with a fluid sample for testing. Optionally a dual-dispensers system having two reagent cartridges and two dispensing lines is included for simultaneous or selective dispensing of reagents for multiple diagnostic measurements. Measured data by sensors positioned in the test channel is used for diagnostic analysis by a microprocessor included in the handle of the device.

The handle of the handheld diagnostic device contains a battery, microprocessor, motor, a driveshaft and a reservoir for storing a reagent for mixing with a body fluid sample. The test head has a notch-like open test channel that traverses the width of the bottom of the test head. A conduit with one-way check valves connects the reagent reservoir to a dispensing opening in a wall of the test channel. A renewable biosensor system having a reusable electrode system and a dispensing means for providing fresh liquid reagent is included in the test head for repeated uses of the test channel and the sensor. The test head has a clear channel cover actuated by the drive shaft for sealing the test channel during mixing and testing as well as for viewing the color change of a colorimetric reaction. Test results are shown in a display unit attached to the handle.

Key features of a diagnostic device of this invention are exemplified by the testing of vagina fluid as follows. When placed inside the vagina channel the vibrating test head stimulates the secretion of vagina fluid and simultaneously draws in a sample fluid into the open channel by a capillary force. At the moment of complete filling of the test channel as detected by a sensor, the control system activates a solenoid which causes an internal elastic pump button to dispense a controlled amount of reagent into the test channel. At the same time the solenoid's actuator rod pushes the drive shaft forward that causes a channel cover to close the open channel. The synchronization of the reagent dispensing and the channel closing is timed to keep the dispensed reagent inside the test channel. During these actions, the vibration of the test channel accelerates the mixing of the reagent with the test sample while the device being removed from the vagina channel. After a predetermined incubation time, the sensors measure the optical density and/or the electrical current level, which represent the concentrations of targeted analytes of the test sample. The microprocessor inside the handle uses the measured data for diagnostic analysis to determine the concentration of a targeted analyte and to provide output to the display unit. The display unit is capable of providing trend data and sending acoustical or visual warning signals. For vagina fluid applications, a diagnostic device may be optionally attached with a dispenser as a multi-functional device for dispensing medication material, spermicide foam or vagina lubricant. Besides body fluids, the features of the diagnostic device of this invention are applicable to the monitoring of targeted components in pourable liquids.

BRIEF DESCRIPTON OF THE DRAWINGS

FIG. 1a is a cross section view of a handheld diagnostic device.

FIG. 1b is an enlarged cross section view of the test head shown in FIG. 1a.

FIG. 2a is a cross section view of a handheld diagnostic device.

FIG. 2b is a cross section view along A-A of FIG. 2a showing a test channel, reagent dispensing opening and two optical sensors.

FIG. 2c is a partial enlarged view of FIG. 2b.

FIG. 2d is a cross section view along B-B of FIG. 2c.

FIG. 2e is a perspective view of a solenoid assembly.

FIG. 2f is a plan view of a handheld diagnostic device of FIG. 2a.

FIG. 3a is a perspective view of a channel cover.

FIG. 3b is a cross section view showing a spring-loaded drive shaft in a test head for mounting the channel cover of FIG. 3a.

FIG. 3c is a side elevation view of a test head showing mounting slots for a channel cover.

FIG. 3d is a side elevation view of a test head with a channel cover engaging with the mounting slots.

FIG. 3e is a cross section view of a drive shaft mechanism and corresponding channel cover engagement at the open position.

FIG. 3f is a cross section view of a drive shaft mechanism and corresponding channel cover engagement at the closed position.

FIGS. 4a, 4b, 4c, 4d, 4e, and 4f are perspective views of a renewable biosensor system with various parts of an electrode system positioned in a test channel.

FIGS. 5a, 5b, 5c, 5d and 5e are section views of a renewable dual biosensor system with its test channel in sequential stages of operation during testing of a fluid sample.

Figure 5A:
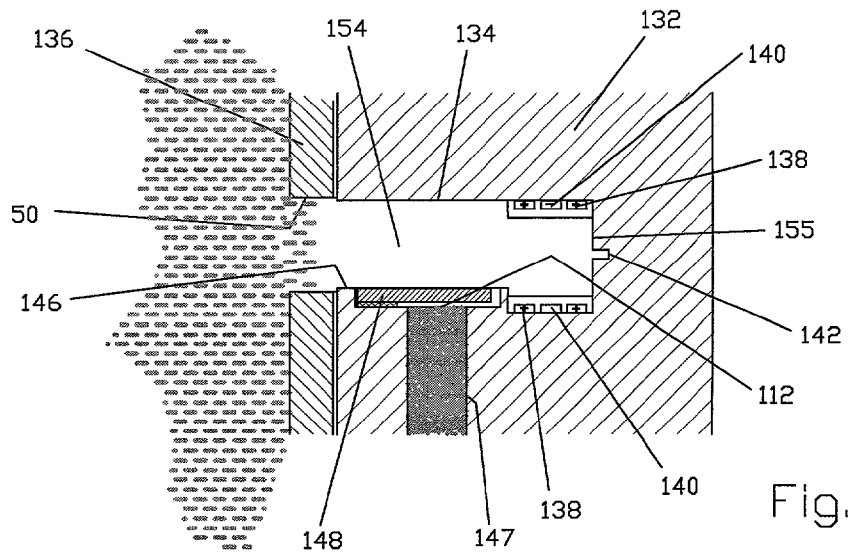
Figure 5B:
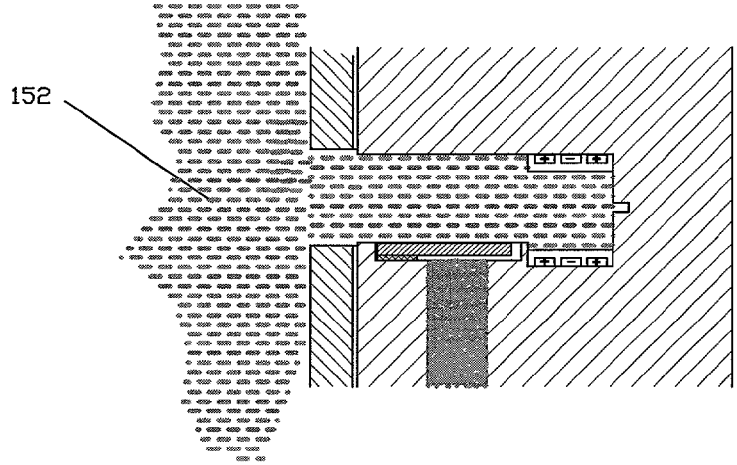
Figure 5C:
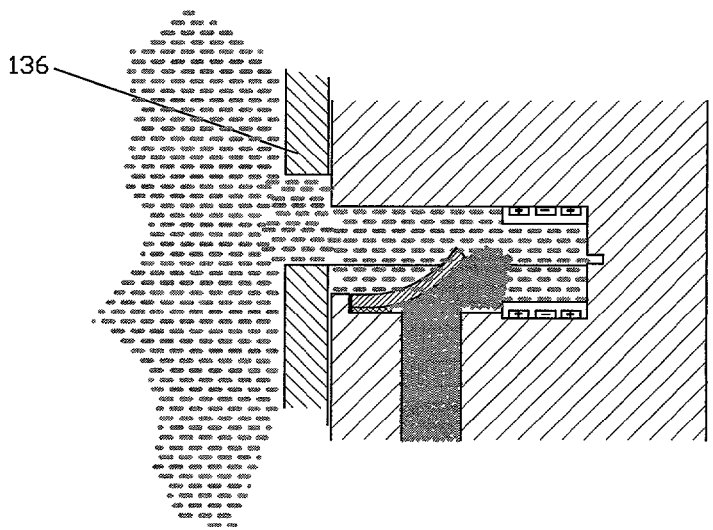
Figure 5D:
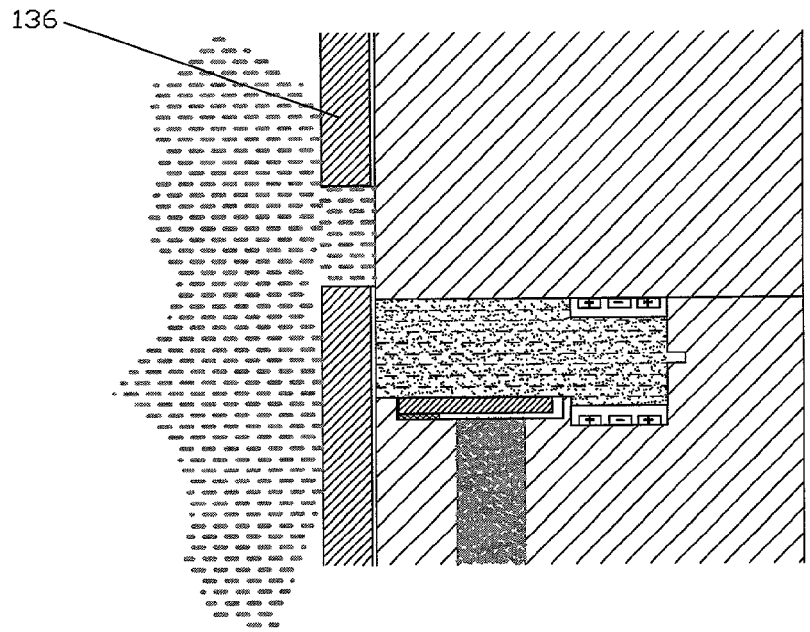
Figure 5E:
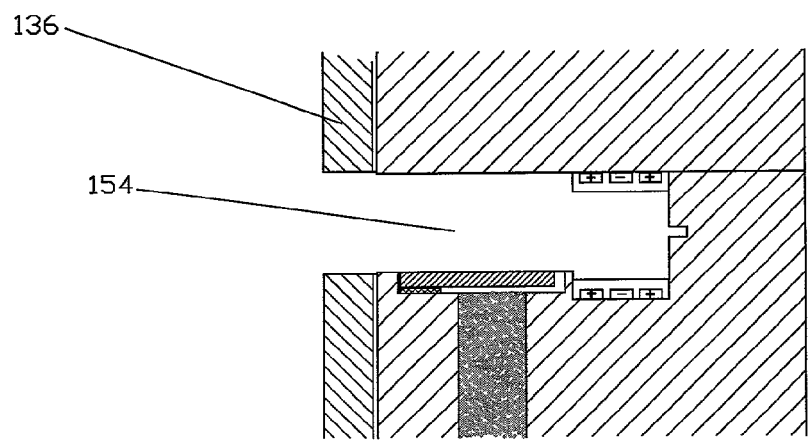
Figure 5F:
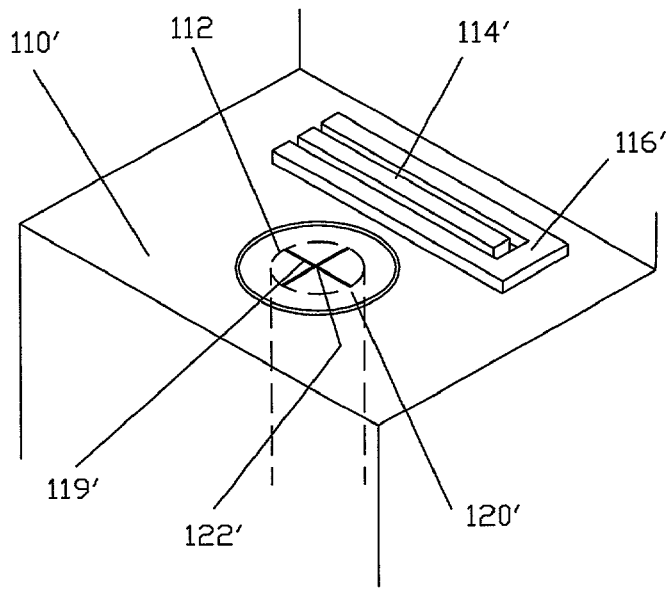

FIG. 5f is a perspective view of a cross-cut slit membrane check valve in a test channel.

Figure 5G:
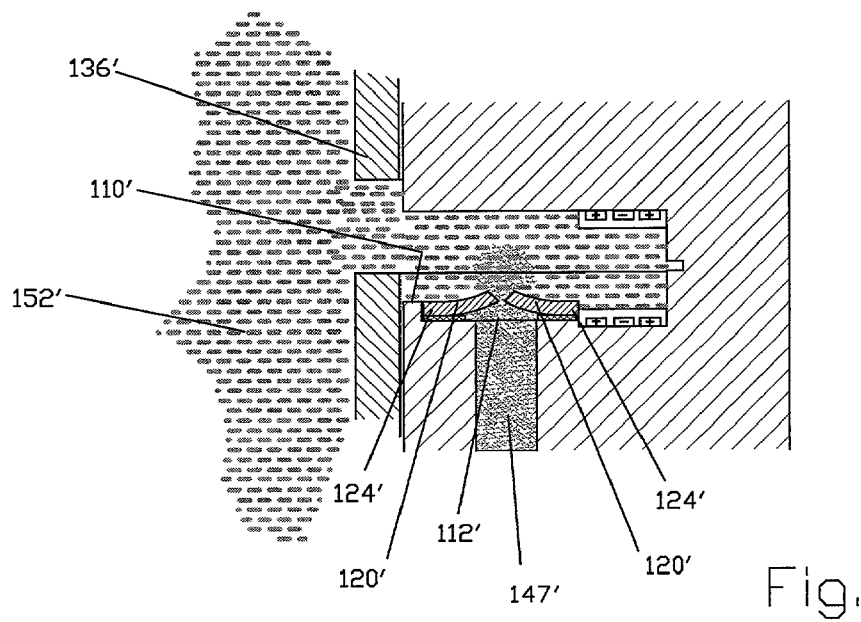

FIG. 5g is a cross-section view of a cross-cut slit membrane being forced open by a dispensing flow into a test channel.

FIG. 5h is a perspective view of a test channel having a renewable biosensor, optical sensors and a detachable channel wall with an electrode system and two pairs of optical sensors.

FIG. 5i is a perspective view of the test channel of FIG. 5h with the detachable wall removed.

FIG. 6a is a perspective view of a test head which has a test channel equipped with sensors and a detachable channel wall.

FIG. 6b is a perspective view of the test head of FIG. 6a with the channel wall detached.

FIG. 7a is a perspective view of a test head which has an open channel matrix positioned on a sensing surface of a test head.

FIG. 7b is a cross section view along A-A of FIG. 7a.

FIG. 7c is an enlarged view of the open test channel matrix of FIG. 7b.

FIG. 8a is a perspective view of a test head which has an open test channel having a reflective optical sensor positioned on a sensing surface of a test head.

FIG. 8b is a cross section view along A-A of FIG. 8a.

FIG. 9a is a cross-section view of a test head having a hydrophobic channel wall.

FIG. 9b is a cross-section view along A-A of FIG. 9a.

FIG. 9c is a top view of FIG. 9a.

FIG. 10a is a cross-section view of a handheld body fluid diagnostic device showing an open test channel, dual reagent dispensers and an electrode system.

FIG. 10b is a cross-section view along A-A of FIG. 10a showing two reagent dispensing openings and two cartridges.

FIG. 10c is a cross-section view along B-B of FIG. 10a.

FIG. 10d is a perspective view of a test channel of FIG. 10a showing a renewable biosensor system with two check valves of reagent dispensers and two optical sensors.

FIG. 10e is a perspective view of a solenoid assembly for the dual reagent dispensers showing in FIG. 10a and FIG. 10b.

FIG. 10f is a cross-section view of FIG. 10a showing the non-dispensing position of the disk actuator of the solenoid of FIG. 10e.

FIG. 10g is a cross-section view of FIG. 10a showing the dual-dispensing position of the disk actuator in pressing on first and second elastic buttons.

FIG. 10h is a cross-section view of FIG. 10a showing the first dispensing position of the disk actuator in pressing on first elastic button.

FIG. 10i is a cross-section view of FIG. 10a showing the second dispensing position of the disk actuator in pressing on second elastic button.

Figure 11A:
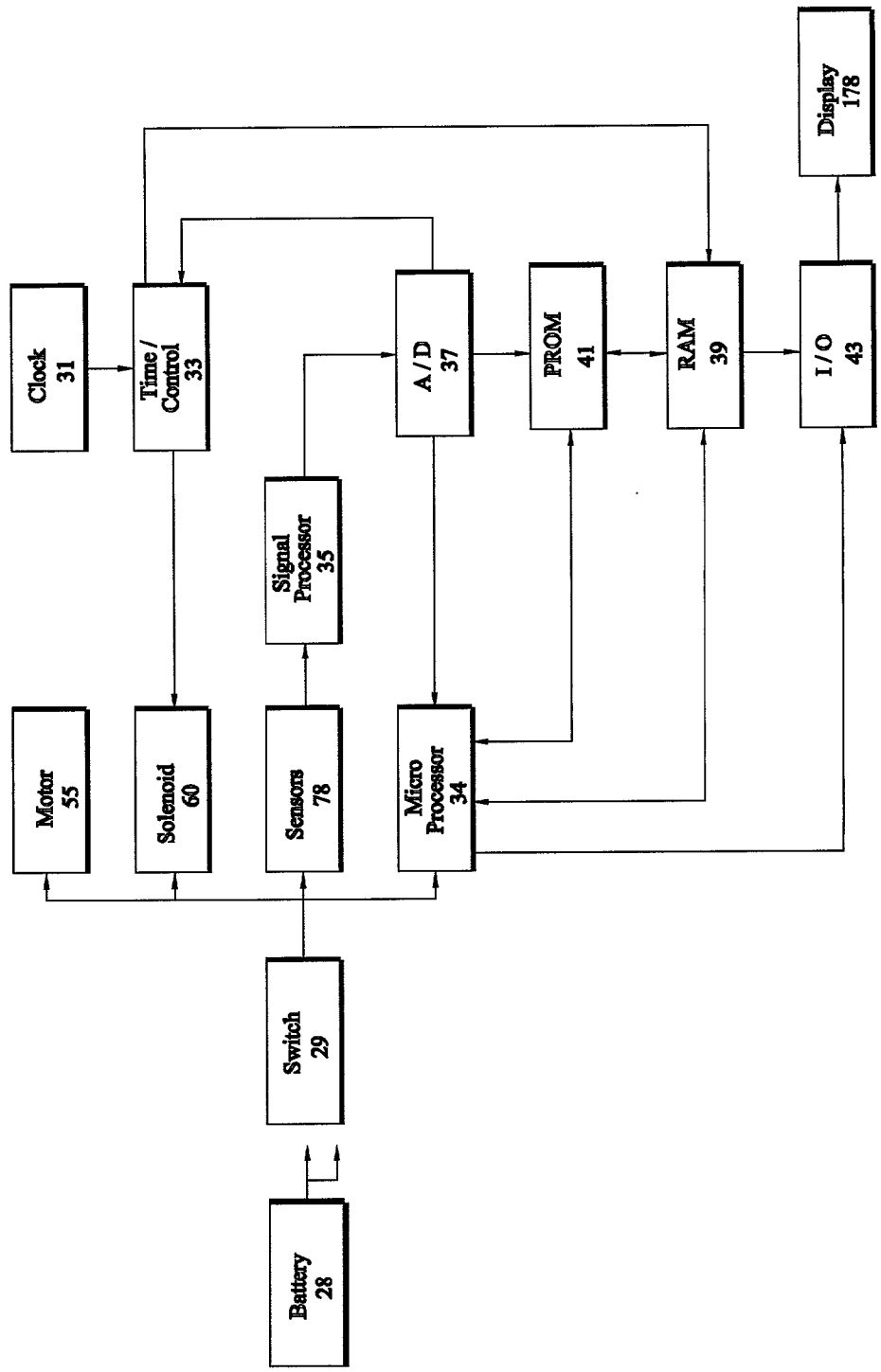
Figure 11B:
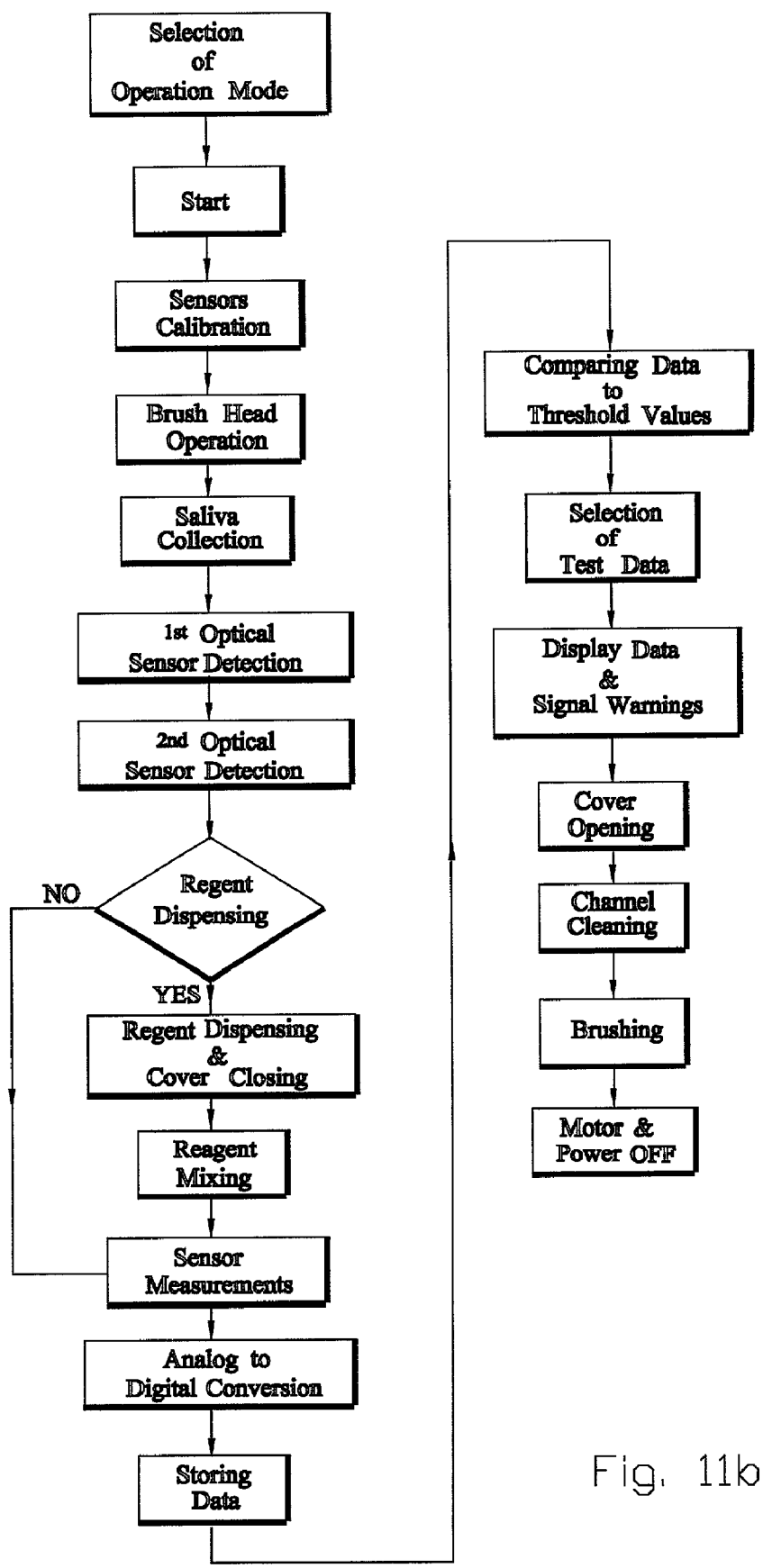

FIG. 11a is a block diagram of the components of a handheld diagnostic device. FIG. 11b is a flow chart of the sequential process steps in the operation of the handheld diagnostic device.

FIG. 12a is a cross-section view of a multi-function handheld diagnostic device having a built-in cream dispenser with an elastic pump button.

FIG. 12b is a plan view of the multi-function handheld diagnostic device of FIG. 12a.

FIG. 12c is a cross-section view of a multi-function handheld diagnostic device of FIG. 12a with the elastic pump button depressed for dispensing.

Figure 13A:
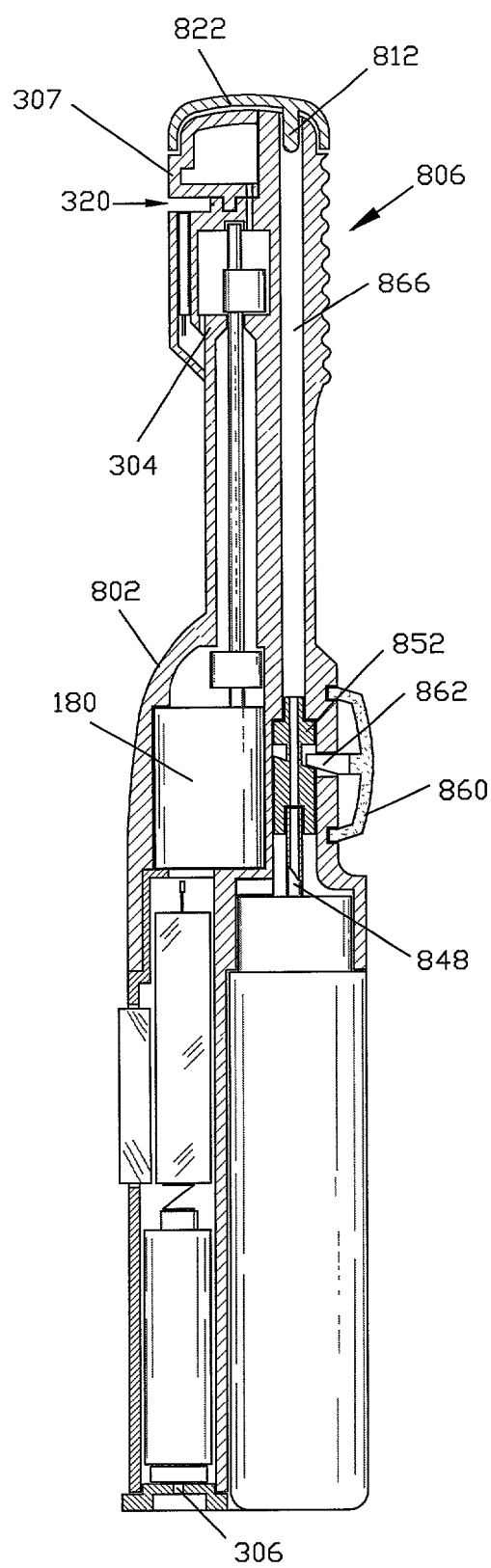

FIG. 13a is a cross-section view of a multi-function handheld diagnostic device having a built-in foam dispenser with an elastic pump button.

Figure 13B:
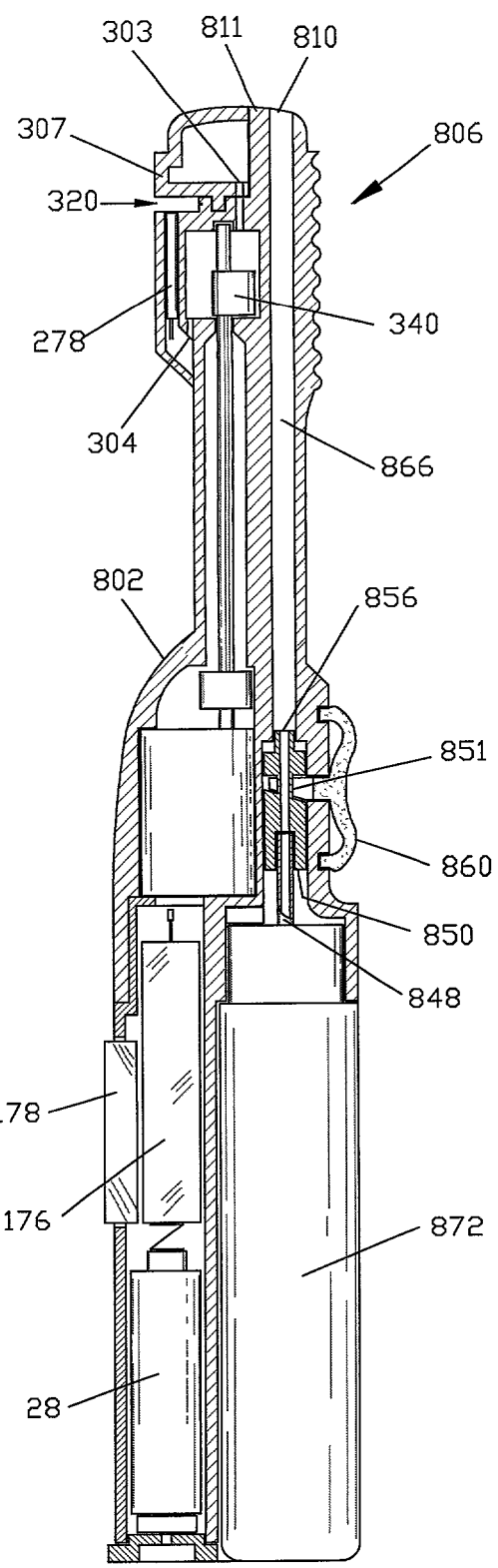

FIG. 13b is a cross-section view of a multi-function handheld diagnostic device of FIG. 13a with the elastic button depressed for dispensing.

DETAILED DESCRIPTION OF THE INVENTION

Figures 1A, 1B:
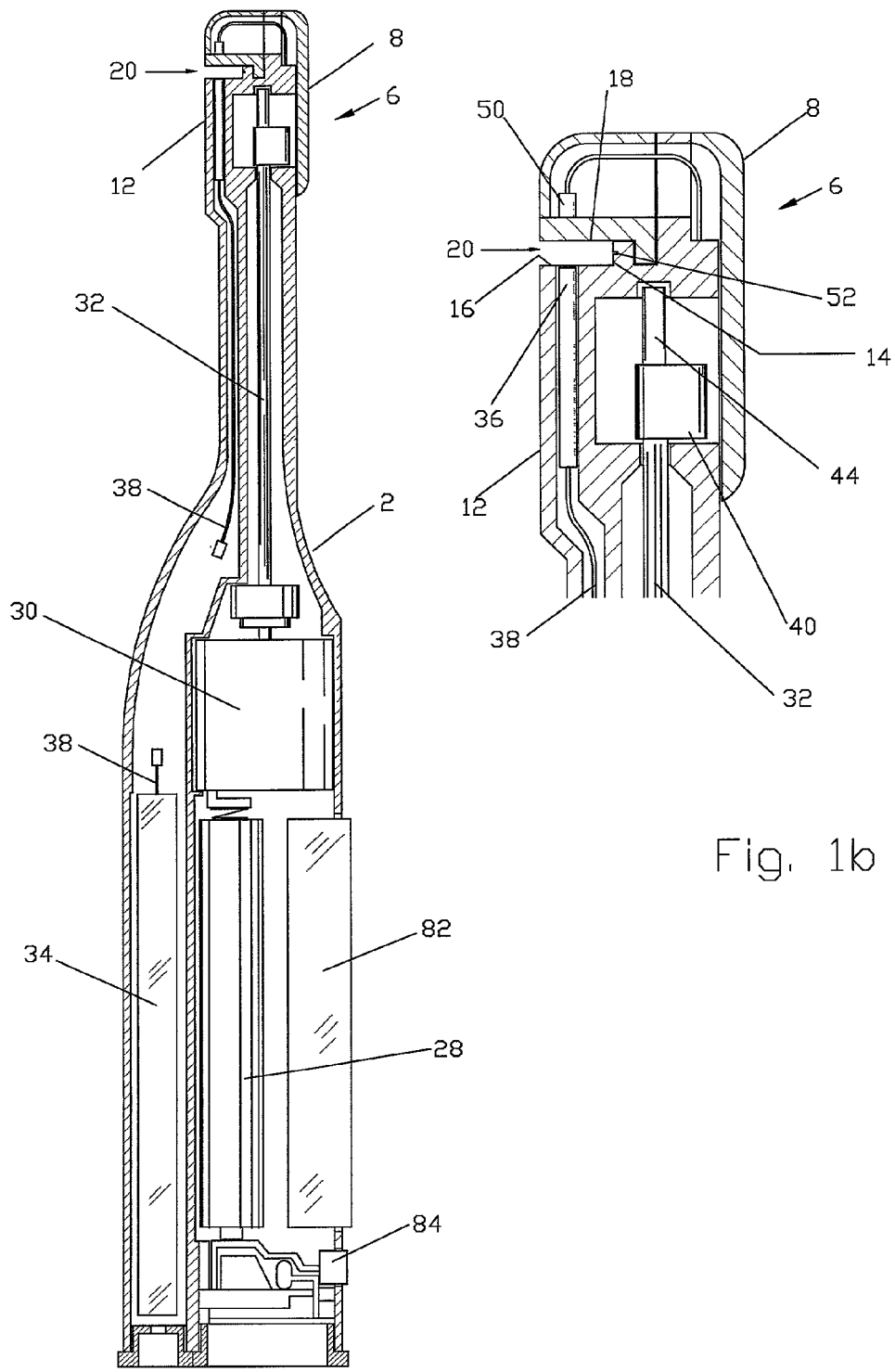
Figure 1C:
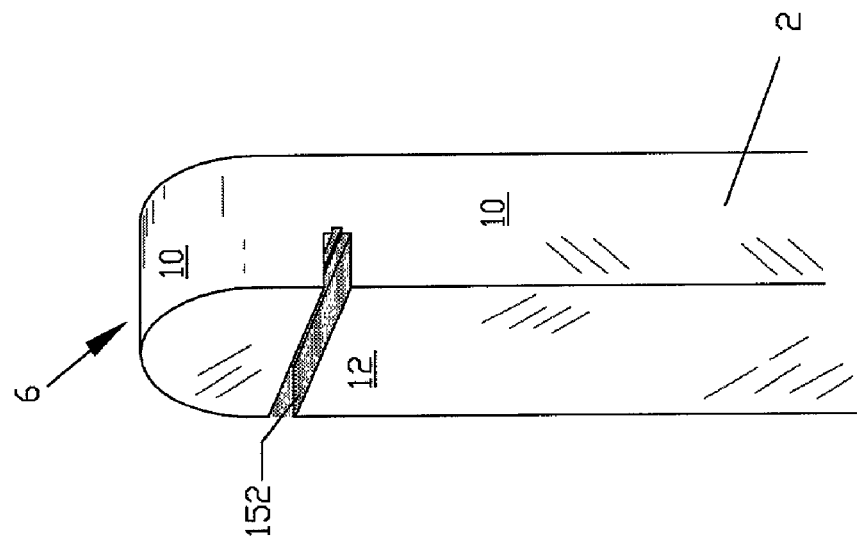
FIG. 1c is a perspective view of the test head shown in FIG. 1b with an empty test channel.

FIGS. 1a, 1b, and 1c show a handheld diagnostic device having handle 2 and test head 6. The test head has top surface 8, edge surface 10 and bottom surface 12. In a preferred embodiment of the invention, open test channel 20 is recessed in bottom surface 12 and traverses the width of test head 6. The open test channel has an upper channel wall 18 and a lower channel wall 16 as well as a base 14, all of which form a front opening 24 which is opposed to base 14. Test channel 20 also has two side openings 26, which are opposed to each other on the edge surfaces 10 of the test head. The channel gap between the upper and the lower channel walls is defined by front opening 24 and side opening 26. It is optimally designed with a width narrow enough for inducing capillary flow and for holding body fluid sample within the open channel but sufficiently wide to allow for the passage of cleaning water to flush out the fluid sample inside the test channel. Vent groove 52 is situated along the length of the channel base 14 in communication with the ambient atmosphere. The width of the vent groove is sufficient to vent entrapped air during filling of the test channel with body fluid but is too narrow for body fluid or water to penetrate into the groove. As shown in FIG. 1b, a sensor pair consisting of light emitter 36 and light detector 50 is positioned across the opposing walls of the test channel. The detection surfaces of the sensor pair are nearly flush with the surfaces of the upper and lower channel walls to facilitate cleaning. Leads 38 connect the sensor and microprocessor 34. Preferably an optically transparent disk (not shown) having high corrosion resistance property is placed in between the sensor surface and the test fluid for protecting the sensor surface from any damages impacting measurement accuracy.

Figure 1D:
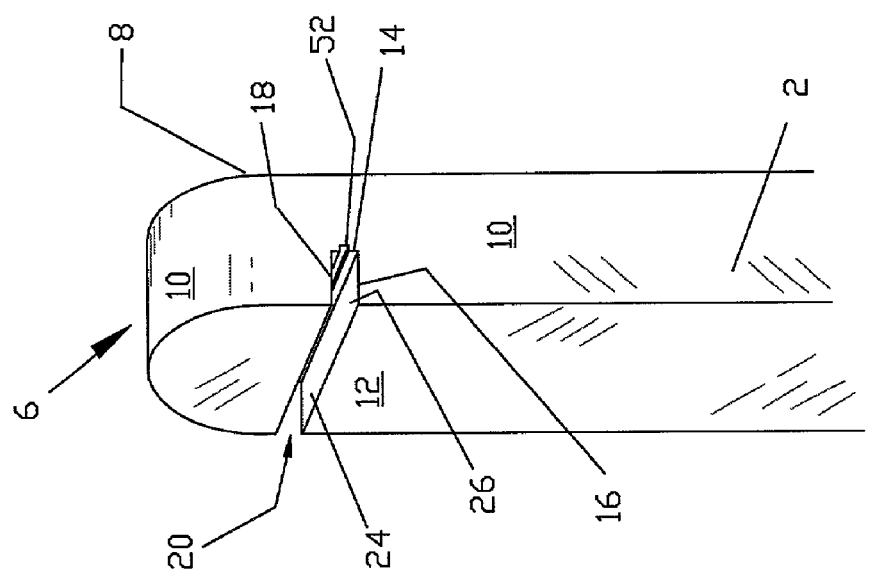
FIG. 1d is a perspective view of the brush head shown in FIG. 1b with a fluid sample in the test channel.

Biased disk 40 and off-centered rod 44, which are mounted on drive shaft 32 driven by a motor 30, impart a vibrating motion to test head 6. In case of collecting saliva sample a test head with vibration is placed in a pool of saliva inside the mouth for drawing in the test sample by the capillary force. For testing an urine sample, the test head is immersed in the urine collected in a cup. For vagina fluid, the test head with vibration is inserted inside the vagina channel. For a blood sample, the test channel draws in blood from finger sticking or is filled with blood droplets ejected from a syringe. In operation, the vibration of the test head 6 generates a low pressure or partial vacuum condition in the vicinity of the open test channel. When immersed in a pool of body fluid, the low-pressure zone immediately next to the open channel induces body fluid to flow into the open channel. The flow of body fluid pushes air out or forces entrapped air into vent groove 52 to release it from the open channel. After the vibration ceases, the test head can be removed from the body fluid pool. The surface tension and the viscosity of the body fluid retain the body fluid 152 inside the narrow open channel as shown in FIG. 1d. The gap across the channel between the sensor pair (not shown in FIG. 1d) is filled thereby forming a continuous body fluid medium for sensor measurement.

The sensor pair is typically either an optical fiber sensor or a electrical conductivity sensor. An optical sensor, either a transmittance or reflective type, is used to measure the opacity or calorimetric response as a representative of a predetermined component in a body fluid sample. The light emitter and the light detector of a transmittance type optical sensor are positioned on opposing walls of the test channel.

The reflective type sensor (not shown in FIGS. 1a and 1b) has a light emitter strand and a light detector strand aligned side-by-side in a housing that is mounted on the lower channel wall (see FIGS. 5h and 5i). Similarly, in the case of a conductivity or amperometric sensor, one configuration is that an electrode (working electrode) and a counter electrode (reference electrode) are positioned across the channel gap to measure the current level as a sensing signal representative of the concentration of a targeted analyte of a body fluid sample. In a preferred embodiment, two sensor pairs are used which can be the same or mixed. The first sensor pair is located close to front opening 24 (shown in FIG. 1c) for early detection and measurement of tested properties of a body fluid sample, and the second sensor pair is located close to base 14 to detect when the channel is completely filled. Complete filling of the test channel is automatically determined as the readings of the second sensor pair start to exceed a predetermined threshold value which is indicative of the complete filling of the gap between the opposing measuring elements of the second sensor pair. This threshold value is established after repeated regular filling of the test channel by a user. The threshold value for the second sensor is the same as the first sensor if they are the same kind of sensor. If different kinds of sensors are used, then each kind has its own threshold value.

Microprocessor 34 controls the timing of the vibration of the test head, the activation of the sensors and the analysis of the output signal from the sensors. The sensors are activated at the same time as the test head vibrates for monitoring the filling of the test channel by the inflow of body fluid. When the second sensor detects the moment of complete filling of the test channel, the readings of both the first and the second sensors are considered valid signals and are stored in the memory of the microprocessor for analysis. Trend data from the analysis is charted in standard display format. An example of trend data is provided in U.S. Pat. No. 3,968,011 by Manautou et al., which shows the peak of optical density of a body fluid two days before menstruation. Using measured data such as that illustrated in the Manautou patent, an algorithm in the microprocessor recognizes the peak and compares the maximum value with an established threshold value. The measured data also is displayed on an LED board to indicate normal data trend and peaks of optical density. If the peak of the displayed data is out of normal range, an acoustic or visual indicator signal is activated to alert the user. To increase the reliability of measured data, two sensors of the same kind are placed near the entrance of a test channel (as shown in FIG. 2b), which has a reagent dispensing opening 86 as shown in FIG. 2b. These sensors are used for cross checking measured data to analyze the consistency and quality of body fluid collection. The body fluid measurements are preferably taken at the same time each day. To adjust for possible effects of body fluid residue in the test channel and sensor signal drifts in the system, the sensor readings are taken automatically prior to the collection of a body fluid sample for calibration purposes. This minimizes or eliminates measurement errors.

For diagnosis of body fluid that requires the use of a reagent for measuring an analyte such as glucose, the handheld diagnostic device includes a reagent-dispensing feature. FIG. 2a shows a handheld diagnostic device having test head 6' with test channel 20' in which a first one-way check valve 66 is positioned between two sensors 78 on top of reagent dispensing opening 86 positioned on the lower channel wall at the end of reagent flow channel 74. Further illustrations of the first check valve and the flow channel are shown in FIGS. 2b, 2c, 2d and 2e. Flow channel 74 is positioned inside of handle 2', which also houses battery 28, microprocessor 34, display 62 and the drive system of the handheld diagnostic device. The display has key buttons for entering the expiration date of a reagent cartridge and the microprocessor is programmed to provide warning signal when the expiration date is approaching.

The overall dispensing mechanism is similar to a that of a dentifrice dispensing toothbrush having a cartridge and an elastic actuator for pumping dentifrice material as described in U.S. Pat. No. 5,909,977 by Kuo. For pumping the reagent, an elastic button 67 having a convex shape and made of resilient rubber is positioned near the exit of a second one-way check valve 71 which is mounted on top of an output opening of refillable cartridge 68. The elastic button is depressed by the forward movement of solenoid disk actuator 58, which is mounted on the solenoid rod 54 of the linear solenoid 60. Edge 61 of disk actuator 58 (FIG. 2e) is in interference position in the path of the forward stroke of disk actuator 58 against the elastic actuator button 67. The elastic button 67 is restored to its original shape as the disk actuator 58 is retracted from the forward position. In operation, the solenoid 60, activated by the microprocessor, moves actuator rod 54 and disk 58 forward so as to depress the elastic button 67. The depressed elastic button applies a hydraulic pressure to the reagent medium in flow channel 70 that keeps the second check valve 71 at a closed position while at the same time forcing a controlled quantity of reagent from flow channel 70 to test channel 20' through opening 86 on the channel wall. The reagent flow forces the first check valve 66 to open and remain at an open position during the dispensing action. At the end of dispensing, the retraction movement of the solenoid actuator releases the elastic button from the depressed position. Due to the requirement of the continuity of flow medium, the resilient recovery of the elastic button to its original shape causes back flow to the cavity under the elastic button. The vacuum force created by the back flow causes the opening of the second check valve 71 and the forward movement of the reagent of the same quantity to flow channel 70 from cartridge 68 which has a follower disk 69 exposed to the atmospheric pressure. During this back flow, the first check valve 66 is at the closed position under atmospheric pressure. The dispensing mechanism automatically dispenses a controlled quantity of reagent with repeated reliability.

The automatic reagent-dispensing feature may be disabled to provide for a non-automatic operation. FIG. 2e shows notch 63 positioned next to edge 61 of disk actuator 58, which is used to depress the elastic button when in the automatic dispensing mode. The profile of the notch is designed to avoid interference contact with the elastic button 67 even when the disk actuator 58 is moved forward with the solenoid actuator rod 54. The non-dispensing mode is enabled by rotating lever 80 on the opposite side of the disk actuator 58 to a different angle. The lever is accessible through a lever slot 81 in the housing as shown in FIG. 2f. Lever slot 81 has two small indents 83 for lodging the lever 80, which is biased against the indents for anchoring.

The required quantity of reagent dispensed into the test channel depends on the volume of the test channel, analyte to be measured as well as the concentration and the clinical/chemical/diagnostic characteristics of the reagent. As measured data depends on the mixing ratio of the reagent and the body fluid in the test channel, maintaining the volume of body fluid inside the test channel is critical for gaining reliable measured data. To ensure no leakage of body fluid from the test channel during the vibration of the test head, a channel cover is used to seal the test channel openings.

FIGS. 3a, 3b, 3c and 3d show a channel cover and mounting features on a test head 98 for sliding the channel cover 88 to the closed position to seal the test channel. FIG. 3a shows a saddle-shaped channel cover 88 having an inlet opening 90 which has the same profile for matching with that of the test channel opening for the closing of the test channel opening. The channel cover has a pair of opposing half-circle-shaped ribs 94 for mounting on drive shaft 106 between a first thrust bearing 102 and a second thrust bearing 104 located within the handheld diagnostic device as shown in FIG. 3b. The mounting is accomplished by insertion of ribs 94 through corresponding slot openings 107 on the two side walls of the test head 98 as shown in FIG. 3c. An additional pair of guide ribs 92 is provided for engaging with the slots 97 on the side walls of the test head as shown in the same figure. These mounting features are snap-on type for the ease of the removal of the channel cover for cleaning after a period of repeated uses. To prevent leakage of the body fluid into the slot opening 107, sealing features are added at the edges of the channel cover. The channel cover is also spring-loaded and biased toward the home or open position where cover opening 90 coincides with the opening of the test channel as shown in FIG. 3d. The biased condition is enabled by pre-compression of spring 100 by first thrust bearing 102 against bushing 103 that is fixed to or an integral part of the handle housing. The length of slots 97 and 107 enables sliding of the channel cover to a closed position where the inlet opening 90 is offset from the channel front opening 24. Preferably the channel cover is injection molded with a clear plastic material for serving as a window for viewing the color change of a fluid sample while undergoing colorimetric reaction during testing.

The translation movement of the drive shaft controls the sliding action of the channel cover. As also shown in FIG. 2a, drive shaft 64 has a D-shaped bottom end 65 that is inserted into a hollow armature shaft 57 of motor 55, which has a rotatable core 56 and an outer stator 59. D-shaped bottom end 65 is pushed by the solenoid actuator rod 54, which is slidable inside the hollow armature shaft 57. FIG. 3e shows the alignment of the channel cover at its home position with respect to its mounting features on the test head. When the solenoid 60 is activated, the solenoid rod 54 is extended so as to push the drive shaft 64 to the forward position. Second bearing 104 pushes the channel cover 88 to the closed position where spring 100 is under full compression. At the same time, disk actuator 58 depresses elastic button 67 which causes the dispensing of reagent to the test channel. FIG. 3f shows the channel cover 88 at the closed position which seals the opening of the test channel. After a period of mixing assisted by the vibration of the test channel, and the acquisition of measured data, the solenoid actuator rod 54 retracts at the command of the microprocessor. The retracted actuator rod 54 causes the backward movement of the drive shaft 64 as the load on the spring 100 is being released. Accordingly, the channel cover is pulled back to its home position again by its linkage with the drive shaft through thrust bearings 102 and 104.

Figure 4A:
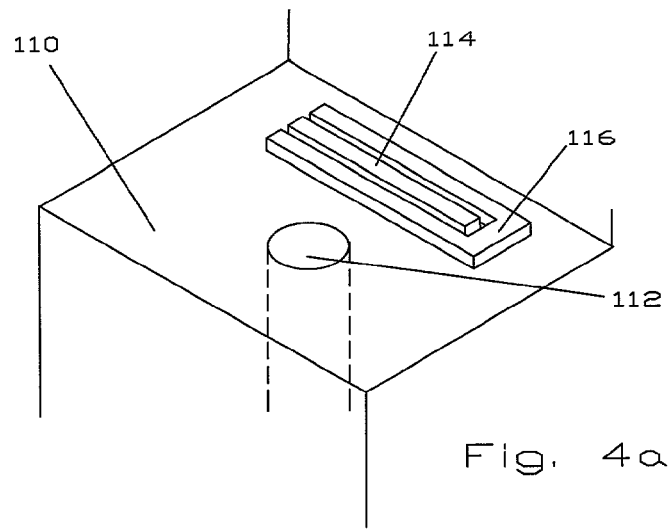
Figure 4B:
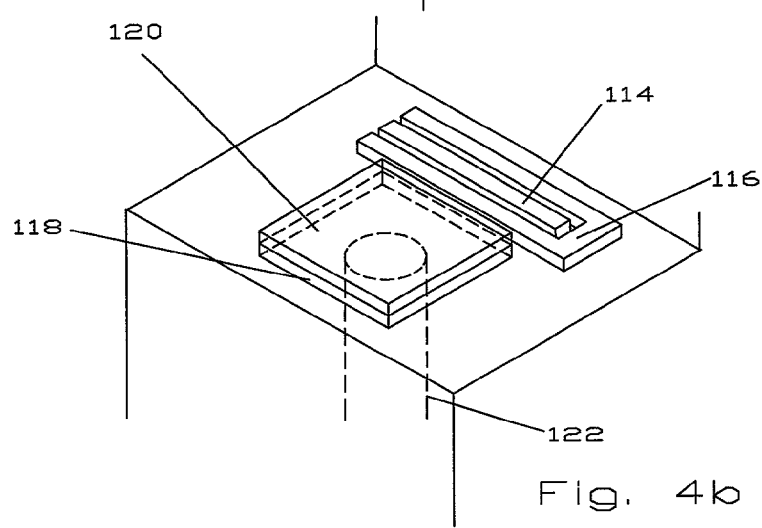
Figure 4C:
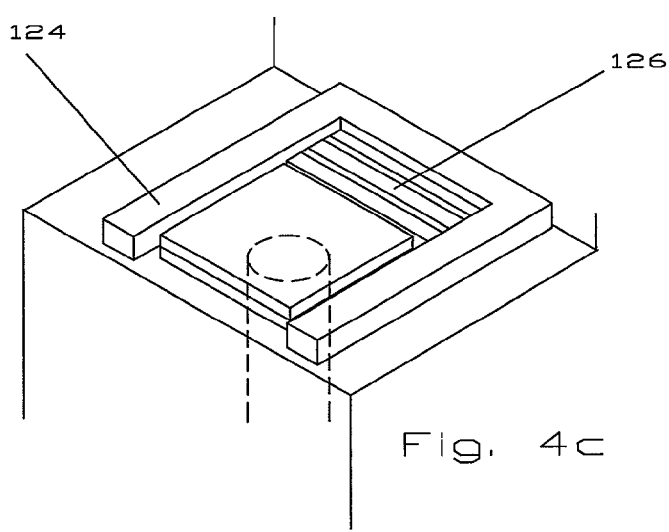
Figure 4D:
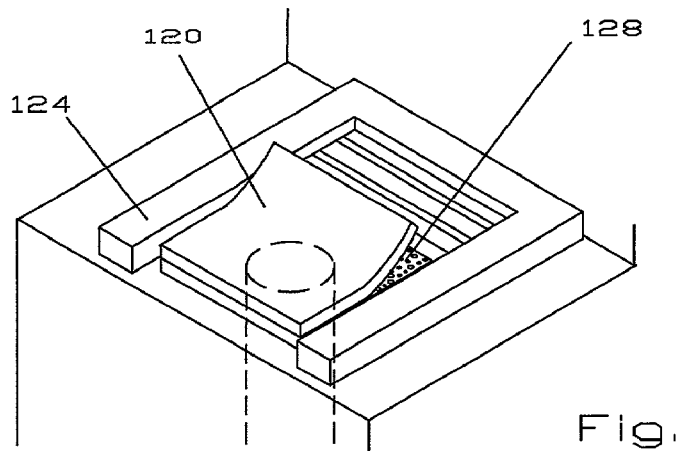
Figure 4E:
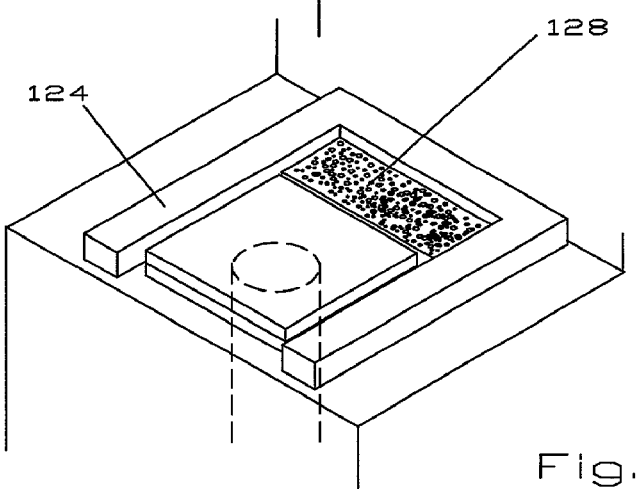
Figure 4F:
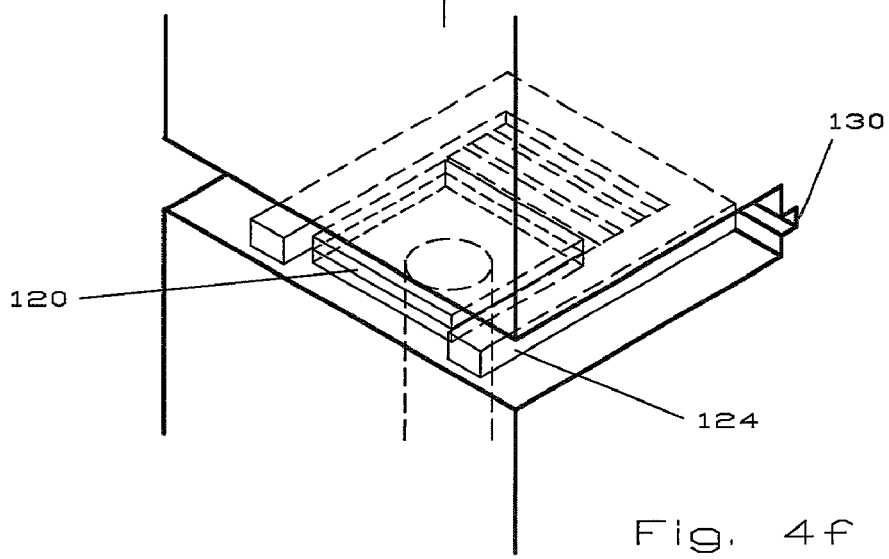

In other applications using a reagent for conductivity or amperometric measurement, a renewable biosensor is used to monitor an analyte in body fluid such as glucose. FIGS. 4a through 4f show components of a renewable biosensor system incorporated into the test channel. The renewable biosensor comprises an electrode system, a reagent dispensing opening 112 and a one-way check valve 120, all positioned on a test channel wall. The electrode system consists of a matrix of electrode 114 and counter electrode 116, which are partially covered by insulation layer 124. The other non-insulated surfaces including measuring surfaces of the electrodes and counter electrodes are preferably coated with a permselective membrane for increasing the linearity of measurement signals and the service life of the electrode system. The insulation layer as shown in FIG. 4c has a pattern of guide walls surrounding the edges of the electrode system and the edge of the check valve for confining the flow of the reagent. The check valve 120 as shown in FIG. 4d, is a resilient plastic film which is fastened at one end as a hinge and the opposite end is openable by a forced reagent flow. The check valve 120 is oriented to open toward the exposed area of the electrode system. FIG. 4e shows a reagent layer 128 deposited on top of the exposed electrode system (non-insulated areas) as the inlet flow of reagent settles at the end of dispensing action and the check valve 120 returns to its original closed position. A predetermined quantity of reagent is consistently dispensed by automatic means so that the thickness of the reagent layer is also consistently formed. In application, the renewable biosensor is incorporated in a test channel having a built-in vent groove 130 for releasing entrapped air as shown in FIG. 4f.

The renewable biosensor is in planar form. FIG. 5a shows two electrode systems with electrodes and counter electrodes, 138 and 140, of the same kind positioned on upper and lower channel walls 134 and 146, across the gap near the base 155 of a test channel 154 and opposing each other. As the reagent is dispensed to the electrode system positioned on the lower channel wall 146 next to the dispensing opening 112, the reagent 147 is to be mixed with the test sample 152 inside the test channel for providing a uniform mixture to be measured by both biosensors and for consistent measurements. The consistency of measured data by the two biosensors at the same time is an indication of the complete filling of the test channel. Since the vibration of the test channel accelerates the mixing of the reagent and the test sample, the test channel is closed by the channel cover 136 during the vibration to prevent body fluid from splashing out of the test channel. For enabling diagnostic measurements at an elevated temperature, a heating element (not shown) can be added to a test channel wall for increasing the temperature of the mixed solution of the reagent and the test sample to a pre-determined operating temperature. The operating temperature is monitored by a temperature sensor mounted in a test channel wall. Both the heating element and the temperature sensor are in communication with the power source and the microprocessor. The incubation time required for the mixing, heating and time for an electrochemical reaction for a specific testing is stored in the microprocessor for the timing control of the diagnostic device.

FIGS. 5a, 5b, 5c and 5d illustrate a sequence involving the actuation of a channel cover with the reagent dispensing for the measurement by a renewable biosensor. FIG. 5a shows the beginning of the intake of a body fluid into the test channel 154 which is immersed in a body fluid pool. For testing a saliva sample, the test channel is immersed in a saliva pool inside the mouth. For blood testing, a test sample is collected from finger sticking by contacting the test channel with the blood pool on the skin or from blood droplets ejected from a syringe. For urine, a test sample is directly collected from urine stream or drawn into the test channel when immersed in a cup of urine. For vagina fluid, the test head is inserted inside the vagina channel to draw in a fluid sample into the test channel. In addition to providing stimulation to the vagina tissues the vibration of the test head results in lower partial vacuum pressure in the immediate vicinity of the test channel opening that, in addition to the capillary effect, induces body fluid to flow into the test channel. During this filling process, channel cover 136 is at the open position until the test channel is completely filled with body fluid sample 152 as shown in FIG. 5b. The timing of complete filling is signaled by the microprocessor, which compares measured data from the two biosensors with predetermined threshold values and acceptable error ranges. At the moment of complete filling, the drive shaft is commanded to move forward. This causes the dispensing of the reagent and the closing of the channel cover. FIG. 5c shows the simultaneous actions of dispensing and partial channel closing. The channel cover may be closed before or after reagent is dispensed into the test channel, depending on the selected time delay and on the positioning of the cover and disk actuator 58 in relation to drive shaft 64 shown in FIGS. 3e and 3f. The timing control of channel closing is optimized to prevent diffusion of the reagent in the fluid sample outside of the test channel. Following closing of the channel, continuous vibration and mixing for a predetermined time period of a few seconds results in a well mixed solution for conductivity or amperometric measurements by the two biosensors.

FIG. 5d shows channel cover 136 at the fully closed position at the end of mixing of the reagent and the body fluid sample. After measured data is transmitted to the microprocessor for analysis and for generating output signals, the test channel is opened by returning the channel cover to its home position, which is achieved by retraction of the solenoid rod. The opened test channel is thus ready for cleaning by using tap or steriled double distilled water or treatment fluid to flush out the mixed test solution and reconditioning the sensors for reuse. In the meantime, the retraction of the solenoid actuator rod 54 and the disk actuator 58 releases the elastic button 67 shown in FIG. 2a. The rebound of the elastic button to its normal position causes reagent to flow from the cartridge into the cavity under the elastic button. There is no back flow of reagent from the flow channel into the cavity because of the viscous resistance caused by the relatively long and narrow configuration of the flow channel. At the time that the resilient second check valve 71 (see FIG. 2a) is closing on the top of the dispensing opening, no residual test solution or cleaning fluid can enter the dispensing opening. Consequently, a cleaned test channel 154 is ready for reuse since the used reagent layer has been washed out and the exposed electrode system is renewed. FIG. 5e shows a renewed test channel that is ready for the next testing cycle with fresh body fluid sample. The test channel is automatically left open for drying by the command of the microprocessor.

Alternately, an elastic membrane valve may be used for sealing of a dispensing opening. FIG. 5f shows the mounting of membrane valve 120' having cross-cut slits 119' on the top of dispensing opening 112, which is positioned on the lower channel wall 110' of a test channel. In a preferred embodiment, membrane valve 120' has four flexible triangular valve segments with apex of each valve segment intercepting at the center 122' of the membrane and the base of the each valve segment is connected forming a continuous outer rim of the membrane valve, which is shown in FIG. 5f at the valve-closed and non-dispensing position. As shown in FIG. 5g the outer rim 124' of membrane valve 120' is fastened to the lower channel wall 110' such that the apex of each valve segment can be bent like a cantilever beam under the pressure of a dispensing flow. FIG. 5h shows that reagent 147' is dispensed through the opening of the membrane valve into the test channel by a reagent dispensing mechanism as described previously in FIG. 2a. The inlet flow of reagent of controlled amount exiting the membrane valve is uniformly mixed with the test sample inside the test channel prior to measurements by sensors. Upon release of the pumping pressure, the elastic valve segment restores to its original flat or unbent configuration. The mixing process is similar to the process as described in from FIG. 5a to FIG. 5e. The clearances between the cross-cut slits 119' are sufficiently small such that the closing position of the membrane valve (shown in FIG. 5f) does not allow for a cleaning agent to penetrate through the wall of the membrane valve to contact the reagent after the testing. The tight clearances for liquid-proof sealing also prevents leakage of the viscous liquid reagent at the non-dispensing position as both the membrane valve and the reagent are being held by an inner vacuum pressure, which holds the reagent inside the flow channel and the cartridge (shown in FIG. 2a). The slit clearance, slit length, wall thickness and the elastic modulus of the membrane valve are determined by the requirements of dispensing a controlled amount of reagent and preventing leakage through the membrane valve.

When the handheld diagnostic device of this invention is not in use, it may be stored in an upright position with the test channel open for ventilation and drying. For storage in a prone position, the open channel may be optionally closed by a slidable plug which is attached to a handheld diagnostic device cover. A plug that is similar to that of the dentifrice-dispensing toothbrush described in U.S. Pat. No. 5,909,977 by Kuo is particularly suitable.

For preventing undesirable complications in some applications associated with blood clots and bacterial infection, coatings serving as surface modifiers can be applied on the surface of a diagnostic device of this invention. Coating which provides a diffusion barrier, such as commercially available SLIP-COAT (trade mark of STS Bio-polymers Inc.) material, can be used for making the surface of a diagnostic device slippery, less prone to infection and clotting, and biocompatible. In addition, after repeated testing and cleaning of the test channel with tap or steriled double distilled water or with a cleaning fluid, the optical sensors and the biosensor in the test channel can still become contaminated with residual body fluid mixture. In order to thoroughly clean the test channel after prolonged repeated use, the upper channel wall of the test channel is optionally detachable. FIG. 5h shows the mounting of a detachable upper channel wall assembly 407 having upper channel wall 134 of test channel 154, which is equipped on lower channel wall 110 with reflective optical sensors 278 and electrode sensor 140. FIG. 5i illustrates lower channel wall 110 of the test channel with upper channel wall assembly 407 detached from the lower channel wall 110, where fiber optics cables 238 are in communication with the microprocessor for the operation of the reflective optical sensors. When upper channel wall assembly 407 is detached, reflective optical sensor 278 and electrode 140 of the renewable biosensor on the lower channel wall are accessible for thorough cleaning. FIG. 6a shows a handheld diagnostic device having handle 2' with upper channel wall assembly 407 attached to test head 406 while FIG. 6b shows upper channel wall assembly 407 detached for cleaning purposes. Upper channel wall assembly 407 is attached to test head 406 by any suitable self-locating, snap-on fastening mechanism. The handle provides battery, microprocessor and display for the operation of the diagnostic testing. A combination of the different sets of sensors provides a broad capability for detecting abnormalities for ensuring the consistency of measured data and for reliability of diagnostics. In the foregoing embodiment, means for including body fluid monitoring and diagnostics capability in a handheld diagnostic device have been described.

Furthermore, for a reagentless diagnosis, a test channel is optionally positioned on a sensing surface of a test head which is a surface equipped with a sensor for contacting a fluid sample for measurements. FIGS. 7a and 7b show a handheld diagnostic device of this invention having test channel matrix 510 positioned on sensing surface 526 of test head 506, which is attached to handle 502. FIG. 7c is an enlarged view of test channel matrix 510 having test channels 520 as shown in FIG. 7b. Test channel matrix 510 consists of an electrode system having electrode 516, counter electrode 514 and insulating layer 524 which covers the external non-measuring surfaces of electrode 516 and counter electrode 514. Electrodes 516 and counter electrode 514 are positioned on sensing surface 526 of test head 506 and are spaced apart so that test channels 520 are formed by the gaps between said electrodes and counter electrodes. As test channel walls 521 are the detecting and measuring surfaces of the electrodes and counter electrode, they are coated with a permselective material for increasing the linearity of measurement signals and service life of the electrodes. Leads 530 and 531 and connectors 538 and 539 carry sensing signals to a microprocessor contained in handle 502. In operation, test channels 520 are filled with a quantity of body fluid by capillary action by immersing test channel matrix 510 in a body fluid pool. The surface tension of the body fluid retains the quantity inside test channels 520 for measurements. Upon command from the microprocessor in handle 502, the electrode system provides a sensing signal representative of targeted component present in a fluid sample. External test channel matrix 510 provides conductivity or amperometric measurements without the use of a reagent.

FIGS. 8a and 8b illustrate a configuration of a test channel 620 positioned on sensing surface 626 of test head 606 of a handheld diagnostic device having handle 2. Test channel 620 is formed by the gap between sensing surface 626 and upper channel wall 624, which is detachable from sensing surface 626 for cleaning. Test channel 620 is equipped with reflective optical sensor 278, which is positioned on sensing surface 626 and opposed to upper channel wall 624. The upper wall is coated with a highly reflective material such as chromium, which is optionally protected by an inert material for preventing corrosion by the test fluid sample. The channel gap between upper channel wall 624 and sensing surface 626 is sufficiently narrow for inducing a capillary flow and to retain a body fluid specimen in test channel 620 by surface tension forces, yet is sufficiently wide for allowing for the passage of tap water or cleaning fluid to flush out the test sample within the channel. Leads 630 transmit sensing signals from reflective optical sensors 278 to a microprocessor contained in the handle 2. In operation, a quantity of body fluid is drawn into test channel 620 by capillary action by immersing the test channel into a pool of body fluid. Surface tension forces retain the fluid sample in the test channel for measurements. Upon command of the microprocessor, optical sensor 278 detects the reflectance signal of the body fluid sample. The signal is transmitted to the microprocessor in handle 2, which produces readable and/or storable signals for the tested property. Both the open test channel having reflective fiber optics sensors and the open test channel having a electrode system sensing means as shown and described in FIGS. 7a and 8a may be placed on the same test head, either on the same surface or on different surfaces, for increasing the measurement capability of a handheld diagnostic device.

Another embodiment of the invention utilizes a hydrophobic air filter to remove pockets of air from a fluid sample in the test channel. Typical hydrophobic air filter methods and materials useful for this purpose are described in US Pat. No. 5,988,426 to Stem and U.S. Pat. No. 6,176,903 to Wamsiedler. While vibration of the test head reduces air pockets within a body fluid specimen, the use of a hydrophobic air filter facilitates removal of any residual air pockets. As shown in FIGS. 9a, 9b, 9c, a hydrophobic filter material 430, which is gas permeable and liquid impermeable, is placed in the upper channel wall of test channel 420 and on leading edge or ceiling 432 of the detachable channel wall assembly 417 mounted on test head 406 of a handheld diagnostic device having handle 2'. The hydrophobic material can also be placed in other selected areas such as in lower channel wall 410. The pore size of the hydrophobic material 430 such as polytetrafluoroethylene is optimally determined to allow for the free passage of air 442 while blocking the passage of the test sample and water through the channel wall. As the capillary flow 440 enters test channel 420, entrapped air pockets tend to migrate to the front and boundary of the progressing flow. Once surfacing on the edges of the flow, the air bubbles burst into the pores of the hydrophobic material 430 and are released from the fluid flow. This venting and filtering function effectively de-gas the sample fluid. Furthermore, the patch of hydrophobic material 430 positioned on ceiling 432 of the detachable channel wall assembly 417 allows pressure equalization between air inside of compartment 433 of the detachable channel wall assembly 417 and the ambient atmospheric pressure. Airflow also occurs through hydrophobic material 430 when the test channel becomes empty after cleaning. When the test head is not in use, the hydrophobic material helps ventilate the test channel during the natural drying process.

There are applications requiring simultaneous dispensing of two non-premixed reagents (two-component reagent) into the test channel for testing a body fluid or dispensing of two different reagents separately for different diagnostics. In all these applications, two cartridges and two dispensing flow lines are needed.

FIGS. 10a and 10b show a handheld diagnostic device having dual dispensers in handle 702 having two dispensing flow lines and two cartridges which contain functional fluids of two different reagents or one reagent and one treatment fluid. Similar to a single reagent dispensing mechanism as described in FIGS. 2a and 2b, each dispensing line of the dual dispensers mechanism has a one-way check valve on top of dispensing opening at the end of flow channel in test channel 720 in test head 706. Each flow channel 74 is in communication with a cartridge 68 in its respective dispensing line and a dispensing flow is enabled by depressing an elastic button 767. FIG. 10c shows a cross-sectional view of the spatial arrangement of the two reagent cartridges 68 inside the handle 702 of the diagnostic device having battery 28, microprocessor 34 and display 62. The corresponding spatial arrangement of the two dispensing openings and accompanying check valves of the dual dispensing system are shown in FIG. 10d. Referring to FIG. 10d the outer edges of the two check valves 121' mounted on the lower channel wall 110' of a test channel (upper channel wall removed in FIG. 10d) are flanged by guide wall 124' which formed wedged shape flow area for guiding reagents exiting from the dispensing openings 112' toward the electrode system. A partition wall 125' is optionally positioned between the two check valves 121' for hindering direct mixing of the two reagents if not desired. The arc-shape pattern of electrodes 114' and 116' is for facilitating the depositing of the reagents in the targeted functional area for conductivity or amperometric measurements. In addition, two reflective fiber optic sensors 278 are positioned near the bottom surface 14 for other signal measurements and for detecting the complete filling of the test channel as described previously.

The simultaneous dispensing action of the two dispensing lines are achieved by using a dual-notch solenoid disk actuator to depress the two elastic buttons, which are positioned at the same distance from the disk actuator. Similar to the mechanism of a single-notch solenoid disk actuator shown in FIG. 2e, FIG. 10e shows the dual-notch disk actuator 758 of the dual dispenser mechanism. The dual-notch disk actuator has two notches 787 and 788 on its edge with the spacing between the two notches the same as that between the two elastic buttons 767 and 768. The sizes and shapes of the two notches 787 and 788 are for accommodating the two elastic buttons 767 and 768 so that when aligned with the elastic buttons the notches do not interfere with the elastic buttons while the dual-notch disk actuator 758 being moved forward and backward. This non-dispense alignment is shown in FIG. 10f, which is a cross-section view of the handle 702 that includes the cartridges, batteries, microprocessor, and display. The simultaneous dispensing position of the dual-notch disk actuator is shown in FIG. 10g. Edge 762 (shown in FIG. 10i) and 763 of dual-notch disk actuator 758 are in interference position in the path of the forward stroke of disk actuator 758 against the elastic actuator button 767 and 768. Both elastic buttons are depressed by the forward movement of dual-notch solenoid disk actuator. The elastic buttons are restored to its original shape as the dual-notch disk actuator 758 is retracted from the forward position. The operation of the simultaneous dispensing mode is similar to that of dispensing a single reagent as described previously. At the command of the microprocessor two reagents are dispensed simultaneously and at the same time the channel cover is being closed by the solenoid action. The mixing and the electrochemical reaction of the two reagents with the test sample generates measurable signals for indicating the analyte concentration and characteristic of the test sample. This dual dispensing capability also enables longer shelf life of a system of two-component reagent as compared to a single pre-mixed liquid reagent system.

In addition, the wide contact edges 762 and 763 on both sides of the notches enable selective depression of the elastic buttons. FIG. 10h and FIG. 10i show the positions of the dual-notch disk actuator selectively pressing on first elastic button 767 and second elastic button 768, respectively. In the above-described dispensing modes, the position of the dual-notch disk actuator 758 is set manually by rotating the knob 780 of disk actuator 758. With the use of the dispensing system of two cartridges and dual-notch actuator, various combinations of applications can be selected. They are: 1) Simultaneous dispensing of two reagents for mixing in the test channel; 2) Individual dispensing of two different reagents for separate measurements; 3) Dispensing of one reagent for measurement and one conditioning fluid for cleaning and calibration; 4) Non-dispensing. With the selective dispensing feature, the same diagnostic device unit of this invention can be used in separate sequence for testing different body fluids with different reagents contained in the handle. In the non-dispensing mode, the same device can also be used for reagent-less testing of a body fluid sample.

After each diagnostic testing, the entire test channel including the sensors and the check valve are cleaned with tap or steriled doubled stilled water or with a treatment liquid.

A block diagram of the electrical components of the handheld diagnostic device of this invention is shown in FIG. 11a. Battery 28 provides power to all the electrical components of the handheld diagnostic device. The switch unit 29 has multiple switches for independently activating motor 55, solenoid 60, sensors 78 and microprocessor 34. A clock 31 provides input to a timer/control unit 33, which controls the timing for activating the solenoid 60. Sensors 78 are connected to a signal processor 35, which amplifies signals received from the sensors and filters the amplified signals as input to the A/D converter 37, which converts the analog signals into digital signals for input to the microprocessor 34. The microprocessor has a random access memory (RAM) unit 39 and a programmable read only memory (PROM) unit 41. The RAM unit contains programming related to the operation of the electrical components and the PROM contains algorithm software for sensor signal calibration and calculation of the concentrations of targeted analytes based on the output of the A/D converter. The information stored in RAM unit 39 is read through I/O 43. Display unit 178 displays trend data of analytes in body fluid samples and provides warning signals if established threshold values are exceeded. A self-explanatory, corresponding flow chart of the operation of the handheld diagnostic device as described herein shown in FIG. 11b.

In another embodiment, a handheld diagnostic device of this invention includes a cream or a foam dispenser. FIG. 12a shows a multi-function handheld vagina fluid diagnostic device having a cream dispenser, which also can be used for dispensing a functional viscous fluid or cream such as a vaginal lubricant or other medication material. The test head 306 includes test channel 320, sensors 278, flow channel 366, and a spout opening 310 positioned in the distal top end surface 311 of the test head for the delivery of a functional viscous material. The spout opening 310 is sealed by cap 322. Detailed descriptions of the dispensing mechanism is set forth in U.S. Pat. No. 5,909,977 by Kuo. Therefore, only a brief description is provided here. The spout opening 310 is connected to a flow channel 366 that is in communication with a pump chamber 204 in handle 302. Pump chamber 204 includes elastic button 168, a one-way check valve 206, and an inlet opening 208 that is connected to cartridge 172 containing cream material. Cartridge 172 has a follower disk 174 for packing the cream material when the cream material is being pumped out. FIG. 12b shows the multi-function handheld diagnostic device of FIG. 12a with the cap removed from the dispensing opening. When elastic button 168 is depressed, the hydraulic pressure causes the one-way check valve 206 to close and the cream material is forced to flow to the spout opening through the flow channel 366. When the elastic button 168 is released, the follower disk 174 moves forward to push the cream material from the cartridge 172 to the pumping chamber to replace the volume dispensed. The depression of the elastic button at the dispensing mode of the device causes the one-way check valve at the closed position. In addition to having microprocessor 176, display 178, battery 28, the handle 302 also includes motor 180 for driving the biased disk 340 for vibrating the test head 306. For the generation of vagina fluid for testing, a ribbed pad 319 is attached to the test head for additional stimulation to the vagina tissues.

In case of dispensing foam material, FIGS. 13a and 13b show a multi-functional handheld vagina fluid diagnostic device having a foam dispenser, which can be used for dispensing spermicide foam or other medication foam material. Referring to FIG. 13a and FIG. 13b, the test head 806 includes a test channel 320, sensors 278 and a spout opening 810 positioned in the distal top end surface 811 of the test head. Detailed descriptions of a pressurized foam dispensing mechanism is well known in the prior art. Therefore, only a brief description is provided here. The spout opening 810 is connected to a flow channel 866 that is inserted with a slidable hollow connector 852 mounted on top of a hollow plunger tube 848 of a pressurized foam canister 872. The slidable hollow connector 852 can be actuated by an elastic button 860, which is bonded to a recess of the handle 802. The upper end 856 of the hollow connector is in sliding engagement with the flow channel 866 of the test head 806 while the lower hollow end is mated with the dispensing tube 848 of the pressurized foam canister 872. The neck section 851 of the hollow connector has a tapered space and an angled surface for engaging with wedged actuator 862 having a corresponding angled surface. Extending from the underside cavity of the elastic button 860, the wedge-shaped actuator 862 has two arms (not shown) for accommodating the neck section 851 when the elastic button is depressed. FIG. 13a shows the elastic button 862 at the non-dispensing or fully extended position. When elastic button 862 is depressed as shown in FIG. 13b, the wedged actuator 862 causes the slidable hollow connector 852 to press down the dispensing tube 848 of the pressurized foam canister 872 to an open or dispensing position. The depressed dispensing tube enables the release of the pressurized foam from the canister to the spout opening in the test head. Upon release of the elastic button, the wedge-shaped actuator retracts and allows the dispensing tube to return to its closed position. Similar to the handheld diagnostic device of FIG. 12a, the handle 802 includes microprocessor, display, and motor for driving the biased disk 340 for vibrating the test head, which is attached with a ribbed stimulation pad.

The present invention has been described in detail with reference to body fluids and preferred embodiments thereof. However, variations and modifications can be implemented within the spirit and scope of this invention. Test fluid samples can be any pourable fluids, such as fruit juices. The configurations of test channel in a test head, the renewable biosensor system, and the operation of the automatic channel as described for a handheld diagnostic device can be applied to any laboratory diagnostic devices for testing body fluids. The open test channel can be in a recess in any surface of a test head and in a form of any elongated cavity with or without a detachable wall for cleaning and the vent groove can be replaced by an aperture for releasing entrapped air. A renewable biosensor in an open test channel may comprise an electrode system and any dispensing means that provides inlet flow of reagent into the open test channel through an opening in a channel wall. A pH sensor, a calorimetric sensor or a spectroscopic, visible and infrared light absorption system can be used in the test channel for measurements. Furthermore, the channel cover and the reagent dispensing can be operated manually rather than automatically by electromechanical means. Also, the fluid diagnostic device of the present invention can be operated with external power source without using a self-contained battery and the microprocessor in the handheld can be in communication remotely via a wireless modem, a cell phone, or a standard phone line with a clinical center for storage of test data and diagnostic analysis by trained medical professionals.

I claim:
1. A body fluid diagnostic device comprising:
a. a handle;
b. a test head attached to the handle, said test head having a test channel which is positioned in a recess in a surface of the test head and said test channel being comprising of a base and opposing upper and lower channel walls which extend from the base and are spaced apart from each other for forming a test channel opening and said test channel being capable of retaining a test sample of body fluid by capillary force;
c. sensing means in communication with the test channel for providing an output sensing signal representative of the tested properties of body fluid collected in said test channel;
d. signal processing means for converting the output sensing signal to readable or storable information, said signal processing means having an input means for receiving the output sensing signal and an output means for producing a signal for information display or storage;
e. a power source attached to said handle for energizing the sensing means and the microprocessor;
f. two cartridges storing functional fluids; and
g. a dispensing means including two elastic buttons and an a disk actuater, said disk actuater contacting the elastic buttons selectively for dispensing at least one functional fluid.

2. The body fluid diagnostic device of claim 1 wherein said dispensing means includes an elastic membrane valve, said elastic membrane valve having flexible valve segments separated by cross-cut slits with slit clearance sufficiently small for liquid-proof sealing of the dispensing opening when said elastic membrane valve being in the closed position.

3. The body fluid diagnostic device of claim 1 wherein:
a. the sensing means is comprised of a renewable biosensor system which includes at least one reusable electrode system having a plurality of electrodes and counter electrodes, said electrode system being positioned on at least one wall of the test channel; and
b. the test channel has an opening in one wall of said test channel for the inlet flow of a controlled quantity of reagent into the test channel for forming a mixture with body fluid, said mixture being removable from the electrode system and from the test channel by a treatment liquid.

4. The body fluid diagnostic device of claim 1 including a driving means for imparting a vibrating motion to the test head.

5. The body fluid diagnostic device of claim 1 including a channel cover for the test channel opening and said channel cover being slidable to its closed and open positions.

6. The body fluid diagnostic device of claim 5 wherein the movement of the channel cover is in response to the dispensing action of a reagent from a cartridge into the test channel.

7. The body fluid diagnostic device of claim 5 wherein the channel cover comprises:
a. a saddle-shaped base with an opening which coincides with the channel opening when the channel cover is in an open position; and
b. guide ribs on the underside of the saddle-shaped base for engaging with slots in the edge surface of the test head and for guiding the sliding movement of the channel cover to its open and closed positions when said guide ribs are engaged in said slots.

8. The body fluid diagnostic device of claim 7 wherein the movement of the channel cover is actuated by a solenoid contained in the handle.

9. A handheld diagnostic device comprising:
a. a handle;
b. a test head having a sensing surface and a reflective fiber optical sensor positioned on the sensing surface, said test head being attached to the handle;
c. a test channel formed by a gap between a detachable channel wall and the sensing surface of said test head, said detachable channel wall having a reflective surface opposing to said sensing surface for reflecting the light beam emitting from the fiber optical sensor, and said test channel being capable of collecting and retaining a fluid sample by capillary force;
d. a signal processing means for converting the output sensing signal of the fiber optical sensor as representative of the tested properties of the fluid sample to readable or storable information, said signal processing means having an input means for receiving the output sensing signal and an output means for producing a signal for information display or storage; and
e. a power source attached to said handle for energizing the sensing means and the signal processing means.

10. A handheld diagnostic device comprising:
a. a handle;
b. a test head attached to the handle having a sensing surface and an electrode system, said electrode system having a plurality of electrodes and opposing counter electrodes positioned on said sensing surface and being spaced apart for forming a gap comprising a test channel between opposing measuring surfaces of said electrodes and counter electrodes whose other non-measuring surfaces being covered with insulating layer, and said test channel being capable of collecting and retaining a test sample by capillary force;
c. a signal processing means for converting the output sensing signal of the electrode system as representative of the tested properties of the fluid sample to readable or storable information, said signal processing means having an input means for receiving the output sensing signal and an output means for producing a signal for information display or storage; and
d. a power source attached to said handle for energizing the sensing means and the signal processing means.

* * * * *